(12) United States Patent  (10) Patent No.:     US 10,424,399 B2
Clark et al.  (45) Date of Patent:     *Sep. 24, 2019

(54) SYSTEMS AND METHODS OF EDITING A POLYGONAL-SHAPED CHEMICAL STRUCTURE HAVING A SET NUMBER OF VERTICES

(71) Applicant: INTEGRATED CHEMISTRY DESIGN, INC., Oceanside, CA (US)

(72) Inventors: John David Clark, Oceanside, CA (US); Mary Catherine Johnson, San Diego, CA (US); Atsuo Kuki, Irvine, CA (US)

(73) Assignee: Integrated Chemistry Design, Inc., Oceanside, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 15/680,065

(22) Filed: Aug. 17, 2017

(65) Prior Publication Data

US 2017/0351846 A1    Dec. 7, 2017

Related U.S. Application Data

(63) Continuation of application No. 13/566,770, filed on Aug. 3, 2012, now Pat. No. 9,754,085.

(Continued)

(51) Int. Cl.
    *G06F 3/0488*    (2013.01)
    *G16C 20/80*    (2019.01)

(52) U.S. Cl.
    CPC ......... *G16C 20/80* (2019.02); *G06F 3/04883* (2013.01); *G06F 2203/04808* (2013.01)

(58) Field of Classification Search
    None
    See application file for complete search history.

(56) References Cited

U.S. PATENT DOCUMENTS 5,249,137 A     9/1993  Wilson et al.
5,379,234 A  *  1/1995  Wilson ................. G16C 20/80
                                                    703/11

(Continued)

FOREIGN PATENT DOCUMENTS

WO    WO 2007/092842 A2     8/2007

OTHER PUBLICATIONS

"Chem & Bio Draw", Version 12.0, CambridgeSoft, Inc., (cover sheet through table of contents), 2009.

(Continued)

*Primary Examiner* — Jennifer N To
*Assistant Examiner* — Joseph R Burwell
(74) *Attorney, Agent, or Firm* — Veros Legal Solutions, LLP

(57)    ABSTRACT

A device comprising a display, a user interface configured to receive gesture input, and a processor is provided. The device is configured to electronically detect, with the user interface, at least one gesture input from the user in an approximately circular motion that traces a substantially closed curve without corners about a point on the user interface. The device is configured to display, on a portion of the display, a polygonal shaped chemical structure symbol representing a polygonal ring of carbon atoms in response to the detecting, the polygonal ring having a set number of vertices representing a set number of carbon atoms. A non-transient computer readable medium having instructions stored thereon that cause a device comprising a display, a user interface configured to receive gesture input, and a processor to perform a method is also provided.

18 Claims, 30 Drawing Sheets

Related U.S. Application Data

(60) Provisional application No. 61/524,721, filed on Aug. 17, 2011.

(56) References Cited

U.S. PATENT DOCUMENTS

| | | | |
|---|---|---|---|
| 5,461,580 | A | 10/1995 | Facci et al. |
| 5,596,689 | A | 1/1997 | Tamura et al. |
| 7,250,950 | B2 | 7/2007 | Smith et al. |
| 7,663,607 | B2 | 2/2010 | Hotelling et al. |
| 7,705,830 | B2 | 4/2010 | Westerman et al. |
| 8,407,578 | B2 | 3/2013 | Boyer et al. |
| 9,754,085 | B2 | 9/2017 | Clark et al. |
| 2007/0192747 | A1 | 8/2007 | Phelan et al. |
| 2008/0165140 | A1 | 7/2008 | Christie et al. |
| 2008/0309632 | A1 | 12/2008 | Westerman et al. |
| 2010/0163316 | A1 | 7/2010 | Chang et al. |
| 2012/0141032 | A1 | 6/2012 | Ouyang et al. |
| 2012/0154440 | A1 | 6/2012 | Nicholls et al. |
| 2013/0111398 | A1 | 5/2013 | Lu et al. |
| 2013/0222265 | A1 | 8/2013 | Smith et al. |

OTHER PUBLICATIONS

"ChemDraw User's Guide", Version 9.01, CambridgeSoft, Inc., (cover sheet through table of contents), Dec. 2004.

"ChemJuice Grande—Basic Structure Drawing", printout page of YouTube video posting from IDBS at http://www.youtube.com/watch?v=mKOcC5bLzdO, uploaded Oct. 3, 2011, printed May 18, 2015.

"Google SketchUp 7 Help", pp. 1-887, 2008.

"IDBS Makes Chemical Structure Drawing Mobile", press release, ID Business Solutions, Ltd., Dec. 9, 2009.

"Introduction to Drawing (iPhone)", http://molmatinf.com/introdrawios.html, Molecular Materials Informatics, Inc., Dec. 9, 2010, retrieved by Archive.org as https://web.archive.org/web/20120413131358/http:l/molmatinf.com/introdrawios.html on Apr. 13, 2012.

"Mobile Molecular DataSheet", http://molmatinf.com/mmdsios.html, Molecular Materials Informatics, Inc., Sep. 23, 2011, retrieved by Archive.org as https://web.archive.org/web/20120403140454/http:l/molmati nf.com/mmdsios.html on Apr. 3, 2012.

"MolPrime+", http://molmatinf.com/molprimeplus.html, Molecular Materials Informatics, Inc., Jan. 23, 2011.

"Overview of Drawing Gestures (iPhone)", http://molmatinf.com/gesturesios.html, Molecular Materials Informatics, Inc., Nov. 3, 2010, retrieved by Archive.org as https://web.archive.org/web/20101118005114/http://molmatinf.com/gesturesios.html on Nov. 18, 2010.

"Polygon Maker", http://www.visguy.com/2006/11/24/polygon-maker/, Nov. 24, 2006.

"Welcome to ChemJuice", http://www.idbs.com/chemjuice, ID Business Solutions, Ltd., Jan. 28, 2010, retrieved by Archive.org as https://web.archive.org/web/20100128211229/http://www.idbs.com/chemjuice/ on Jan. 28, 2010.

ACD/ChemSketch, Version 12.0 for Microsoft Windows, Reference Manual, Comprehensive Interface Description. 2010. Advanced Chemistry Development, Inc. pp. 1-189.

Brecher, Jonathan. "Graphical Representation Standards for Chemical Structure Diagrams (IUPAC Recommendations 2008)." Pure App. Chem vol. 80, No. 2, pp. 277-410, 2008.

Clark, "Basic primitives for molecular diagram sketching", Journal of Chem informatics 2:8, pp. 1-20, 2010.

Hammond et al., "LADDER, a sketching language for user interface developers", Computers & Graphics 29, pp. 518-532, 2005.

Hardesty, "Sketch-interpreting software", MIT News, Feb. 19, 2010.

Li et al., Personal Experience with Four Kinds of Chemical Structure Drawing Software: Review on Chem Draw, ChemWindow, ISIS/Draw, and ChemSketch, J. Chem. Inf. Comput. Sci. 44:1886-1890 (2004).

Logtenberg, "Multi-user interaction with molecular visualizations on a multi-touch table", MSc thesis, Human Media Interaction Group, University of Twente, Aug. 11, 2009.

Mills, "Chem Draw Ultra 10.0", Journal of American Chemical Society, v. 128, n. 41, pp. 13649-13650, 2006.

Ouyang et al., Chem Ink: A Natural Real-Time Recognition System for Chemical Drawings, Proceedings of the 16th International Conference on Intelligent User Interfaces (I U 1'11 ), pp. 267-276, Feb. 16, 2011.

Ouyang et al., "Learning from Neighboring Strokes: Combining Appearance and Context for Multi-Domain Sketch Recognition", Proceedings of the 22nd International Conference on Neural Information Processing Systems (NI PS'09), pp. 1401-1409, 2009.

Ouyang, "Recognition of Hand Drawn Chemical Diagrams", Master's thesis, MIT, 2007.

Paulson et al., "PaleoSketch: Accurate Primitive Sketch Recognition and Beautification", Proceedings of the 13th International Conference on Intelligent User Interfaces (IUI'08), pp. 1-10, Jan. 13, 2008.

Plimmer et al., "A Toolkit Approach to Sketched Diagram Recognition", Proceedings of Human-Computer Interfaces (HCI'07), 2007.

Sande, "Found Footage: Instaviz, graph sketching app for an iPhone", https://www.engadget.com/2008/12/09/found-footageinstaviz-graph-sketching-app-for-iphone/, Dec. 9, 2008.

Sezgin et al., "Sketch Based Interfaces: Early Processing for Sketch Understanding", Workshop of Perceptive User Interfaces (PUI'01 ), pp. 1-8, 2001.

Shine et al., "ChemPad3 a tutorial", http://www.chempad.org, pp. 1-10, May 21, 2008.

Sinex et al., "ChemSketch: A Guide to Drawing Chemical Structures", ChemSketch Version 5, http://acdlabs.com, Jan. 2004.

Tenneson et al., "Chem Pad: Generating 30 Molecules From 20 Sketches", SIGGRAPH '05, 2005.

Williams, "Mobile apps for chemistry in the world of drug discovery", Drug Discovery Today, v. 16, n. 21/22, pp. 928-939, Nov. 2011.

Search Report for Great Britain Application No. 1214209.7 dated Dec. 7, 2012.

* cited by examiner

Before Selection:

After Selection:

Before Selection:

After Selection:

Before Rotation:

After Rotation:

Before Translation:

After Translation:

Before Translation:

After Translation:

Before Scaling:

After Scaling Double Tap:

Bond Selection:

Saturated Ring Appended:

Atom Selection:

Spiro Ring Appended:

Unsaturated Ring Generation:

Bond Selection:

Unsaturated Ring Appended:

Two Atom Selections:

Ring Formation:

Two Atom Selections, from Two Distinct Molecules:

Bond Formation:

Select Atom:

Chain Appended to the Right:

Select Atom:

Methyl Group Sprouted:

Select Atom:

Append Gem-dimethyl Group:

Group Position Before Alignment:

Group Position After Alignment:

Pre-isomerization:

Post-isomerization:

Atom Selection:

Edit Formal Charge:

Atom Selection:

Group Abbreviation Addition:

Group Abbreviation Selection:

Group Abbreviation Edit:

Molecule Selection:

Reaction Arrow Draw:

Molecule Selection:

Retrosynthetic Arrow Generation:

SYSTEMS AND METHODS OF EDITING A POLYGONAL-SHAPED CHEMICAL STRUCTURE HAVING A SET NUMBER OF VERTICES

RELATED APPLICATIONS

This application is a continuation of U.S. non-Provisional application Ser. No. 13/566,770, filed Aug. 3, 2012, which claims priority to U.S. Provisional Application 61/524,721, filed on Aug. 17, 2011. Both of these applications are incorporated by reference herein in their entireties.

BACKGROUND

Field of the Invention

The invention relates to editing and creating chemical structures on a touch-screen device.

Description of the Related Art

There are many occasions in which editing a molecular structure on a computer is necessary in the process of designing and studying chemical compounds useful in the following fields: agricultural, analytical, biochemical, biotechnology, food and flavor, pharmaceutical, legal, medicinal, oil and petroleum, polymer, pulp and paper, and textile or in chemistry education. Traditionally, creating and editing structures is done primarily using the mouse to indicate locations of new atoms and bonds, and the keyboard to indicate element types associated with the atoms. Complex chemical structure drawings are built up by selecting predefined templates from vast sheets of templates, and templates are linked together via atoms and bonds. An example of a traditional editing application is shown by Facci et al. in U.S. Pat. No. 5,461,580.

With modern devices having touch screens, and with multi-touch capability, editing molecular structures can be made easier by utilizing these new technologies. There are a number of touch-screen gestures that have standard interpretations in other software applications. Generally, these gestures have descriptive names, and where appropriate, those names will be used here. It should be understood that any reference to such names is not limiting of the types of gestures which may be used in the various embodiments.

SUMMARY OF THE INVENTION

Various embodiments of systems, methods and devices are within the scope of the invention. Some features are described herein related to editing and creating chemical structures on a touch-screen device. These features incorporate new devices and technologies enabling touch-screen capability. The use of these new technologies can be described as using a language of gestures which are then interpreted to perform functions in editing a molecular structure.

Various aspects of embodiments within the scope of the invention are described below. The aspects described herein may be embodied in a wide variety of forms and any specific structure and/or function described herein is merely illustrative. Based on the present disclosure one skilled in the art will appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structures and/or functionality in addition to or other than one or more of the aspects set forth herein.

In one implementation, a device comprises a display, a touch screen user interface, and a processor. The device may be configured to electronically detect, with the touch screen user interface, at least one fingertip in contact with the touch screen and moving over the surface of the touch screen in an approximately circular motion, and display, on the display, a chemical structure symbol representing a ring of carbon atoms in response to the detecting. The device is configured to display a chemical structure symbol representing a saturated ring of carbon atoms in response to the detecting. The chemical structure symbol may be a regular polygon. The device may be configured to electronically detect two fingertips simultaneously in contact with the touch screen and moving over the surface of the touch screen in an approximately circular motion. In this case, the device may configured to display a chemical structure symbol representing an unsaturated ring of carbon atoms in response to the detecting, which may be a regular polygon with line segments or a circle on the interior thereof. The device may be configured to display a number wheel, and to detect a fingertip touch on a particular number on the displayed number wheel, and wherein the displayed regular polygon has the particular number of vertexes.

In another implementation, a non-transient computer readable medium has instructions stored thereon that cause a touch-screen enabled device comprising a display, a touch screen user interface, and a processor to perform a method comprising the acts of electronically detecting, with the touch screen user interface, at least one fingertip in contact with the touch screen and moving over the surface of the touch screen in an approximately circular motion, and displaying, on the display, a chemical structure symbol representing a ring of carbon atoms in response to the detecting. The displaying may comprise displaying a chemical structure symbol representing a saturated ring of carbon atoms in response to the detecting. The chemical structure symbol is a regular polygon. The detecting may comprise detecting two fingertips simultaneously in contact with the touch screen and moving over the surface of the touch screen in an approximately circular motion. In this case, the displaying may comprise displaying a chemical structure symbol representing an unsaturated ring of carbon atoms in response to the detecting, which may be a regular polygon with line segments or a circle on the interior thereof. The method may further comprise displaying a number wheel, detecting a fingertip touch on a particular number on the displayed number wheel, and wherein the regular polygon has the particular number of vertexes.

In another implementation, a device comprises a display, a touch screen user interface, and a processor. The device may be configured to electronically detect, with the touch screen user interface, at least one fingertip in contact with the touch screen user interface and moving over the surface of the touch screen user interface in an approximately straight line, and display, on the display, a chemical structure symbol representing an alkyl chain of a selected length or an increase in length of an already displayed alkyl chain in response to the detecting. The direction of the moving may define the direction of at least one bond of the alkyl chain. The device may be configured to electronically resolve the direction of the moving into one of at least six directions.

In another implementation, a non-transient computer readable medium has instructions stored thereon that cause a touch-screen enabled device comprising a display, a touch screen user interface, and a processor to perform a method comprising the acts of electronically detecting, with the touch screen user interface, at least one fingertip in contact with the touch screen user interface and moving over the surface of the touch screen user interface in an approximately straight line, and displaying, on the display, a chemical structure symbol representing an alkyl chain of a selected length or an increase in length of an already displayed alkyl chain in response to the detecting. The direction of the moving may define the direction of at least one bond of the alkyl chain. The detecting may resolve the direction of the moving into one of at least six directions.

In another implementation, a device comprises a display, a touch screen user interface, and a processor. The device may be configured to electronically detect, with the touch screen user interface, at least one fingertip in contact with the touch screen at or near a displayed atom of a displayed chemical structure and display, on the display, one or more buttons. It may also be configured to electronically detect, with the touch screen user interface, at least one fingertip in contact with the touch screen at or near one of the one or more buttons and display, on the display, a symbol representing a methyl group bonded to the displayed atom in response to the detecting.

In another implementation, a non-transient computer readable medium having instructions stored thereon that cause a touch-screen enabled device comprising a display, a touch screen user interface, and a processor to perform a method comprising the acts of electronically detecting, with the touch screen user interface, at least one fingertip in contact with the touch screen at or near a displayed atom of a displayed chemical structure, and displaying, on the display, one or more buttons. The instructions may also cause the device to electronically detect with the touch screen user interface, at least one fingertip in contact with the touch screen at or near one of the one or more buttons and display, on the display, a symbol representing a methyl group bonded to the displayed atom in response to the detecting.

In another implementation, a device comprises a display, a touch screen user interface, and a processor. The device may be configured to display a symbol representing a first geometric isomer of a chemical structure, electronically detect, with the touch screen user interface, at least two fingertips simultaneously in contact with the touch screen user interface and moving over the surface of the touch screen user interface in an approximately straight line; and display, on the display, a second different geometric isomer of the chemical structure symbol in response to the detecting. The first geometric isomer may be a cis or trans isomer; and the second geometric isomer may be a trans or cis isomer.

In another implementation, a non-transient computer readable medium has instructions stored thereon that cause a touch-screen enabled device comprising a display, a touch screen user interface, and a processor to perform a method comprising the acts of displaying a symbol representing a first geometric isomer of a chemical structure, electronically detecting, with the touch screen user interface, at least two fingertips simultaneously in contact with the touch screen user interface and moving over the surface of the touch screen user interface in an approximately straight line, and displaying, on the display, a second different geometric isomer of the chemical structure symbol in response to the detecting. The first geometric isomer may be a cis or trans isomer; and the second geometric isomer may be a trans or cis isomer.

In another implementation, a device comprises a display, a touch screen user interface, and a processor. The device may be configured to electronically detect, with the touch screen user interface, at least one fingertip in contact with the touch screen user interface and moving over the surface of the touch screen user interface in an approximately straight line, and display, on the display, a chemical structure symbol representing a reaction arrow in response to the detecting. The device may be configured to display a unidirectional reaction arrow in response to detecting a single fingertip in contact with the touch screen user interface and moving over the surface of the touch screen user interface in an approximately straight line, and the device may also be configured to display a retrosynthetic reaction arrow in response to detecting two fingertips simultaneously in contact with the touch screen user interface and moving over the surface of the touch screen user interface in an approximately straight line.

In another implementation, a non-transient computer readable medium has instructions stored thereon that cause a touch-screen enabled device comprising a display, a touch screen user interface, and a processor to perform a method comprising the acts of electronically detecting, with the touch screen user interface, at least one fingertip in contact with the touch screen user interface and moving over the surface of the touch screen user interface in an approximately straight line and displaying, on the display, a chemical structure symbol representing a reaction arrow in response to the detecting. The instructions may cause the device to display a unidirectional reaction arrow in response to detecting a single fingertip in contact with the touch screen user interface and moving over the surface of the touch screen user interface in an approximately straight line, and may cause the device to display a retrosynthetic reaction arrow in response to detecting two fingertips simultaneously in contact with the touch screen user interface and moving over the surface of the touch screen user interface in an approximately straight line.

In another implementation, a device comprises a display, a touch screen user interface, and a processor. The device may be configured to electronically detect, with the touch screen user interface, at least one fingertip in contact with the touch screen user interface and moving over the surface of the touch screen user interface in a check mark formed by two approximately straight non-parallel lines joined at a vertex and display, on the display, a chemical structure symbol representing a gem dimethyl group in response to the detecting. The device may be configured to display the gem dimethyl group attached to a pre-selected atom.

In another implementation, a non-transient computer readable medium has instructions stored thereon that cause a touch-screen enabled device comprising a display, a touch screen user interface, and a processor to perform a method comprising the acts of electronically detecting, with the touch screen user interface, at least one fingertip in contact with the touch screen user interface and moving over the surface of the touch screen user interface in a check mark formed by two approximately straight non-parallel lines joined at a vertex and displaying, on the display, a chemical structure symbol representing a gem dimethyl group in response to the detecting.

In another implementation, a device comprises a display, a touch screen user interface, and a processor. The device may be configured to display a symbol representing an atom or group of atoms attached to another atom of a chemical structure in a first direction, electronically detect, with the touch screen user interface, at least two fingertips simultaneously in contact with the touch screen user interface and moving over the surface of the touch screen user interface in an approximately straight line, and display, on the display, the atom or group of atoms attached to the other atom of the chemical structure in a second different direction in response to the detecting.

In another implementation, a non-transient computer readable medium has instructions stored thereon that cause a touch-screen enabled device comprising a display, a touch screen user interface, and a processor to perform a method comprising the acts of displaying a symbol representing an atom or group of atoms attached to another atom of a chemical structure in a first direction, electronically detecting, with the touch screen user interface, at least two fingertips simultaneously in contact with the touch screen user interface and moving over the surface of the touch screen user interface in an approximately straight line, and displaying, on the display, the atom or group of atoms attached to the other atom of the chemical structure in a second different direction in response to the detecting.

In another implementation a system for creating and/or manipulating symbols representing chemical structures comprises a display device comprising a touch-screen user interface, a processor coupled to the display device and configured to detect touch-screen gestures performed by a user on the touch-screen user interface and to display selected symbols representing chemical structures in response to the detected touch-screen gestures. In this implementation, the processor is configurable by the user to operate in a first mode or a second mode. In the first mode the processor is configured to display an alkyl chain on the display in response to detecting at least one fingertip in contact with the touch screen and moving over the surface of the touch screen in an approximately straight line. In the second mode the processor is configured to display a reaction arrow on the display in response to at least one fingertip in contact with the touch screen and moving over the surface of the touch screen in an approximately straight line.

DETAILED DESCRIPTION OF THE PREFERRED EMBODIMENT

Embodiments of the invention will not be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable qualities or which is essential to practicing the inventions herein described.

Figure 1A:
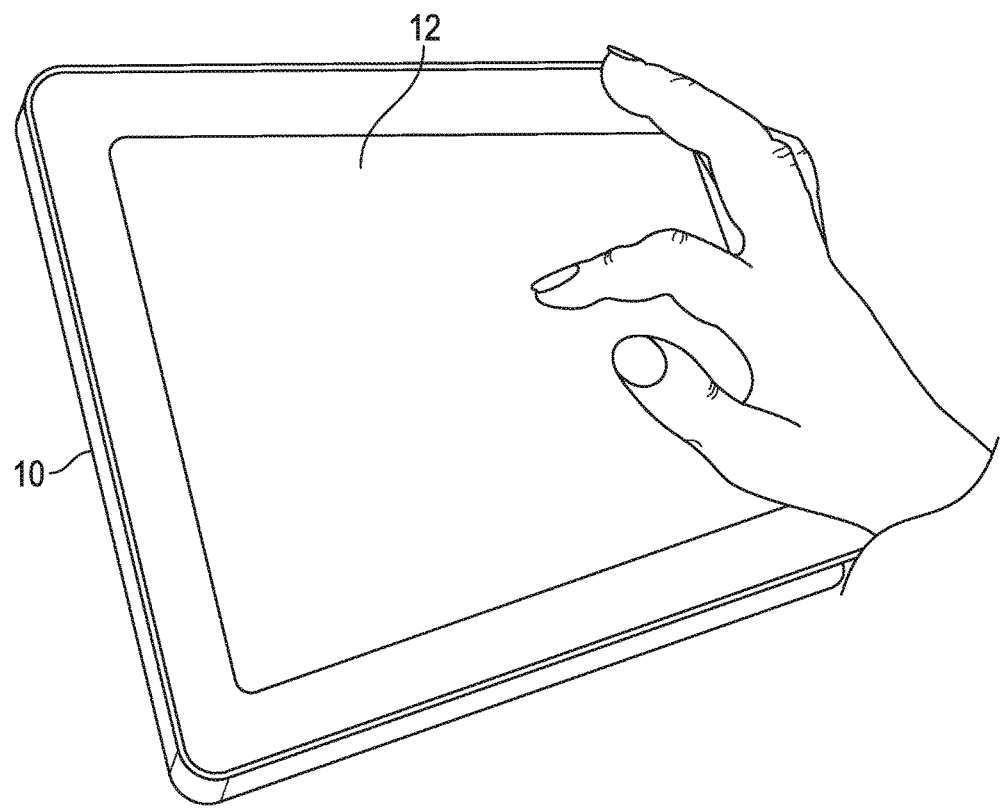
FIG. 1A is a perspective view of a computing device with a display and touch-screen interface.
Figure 1B:
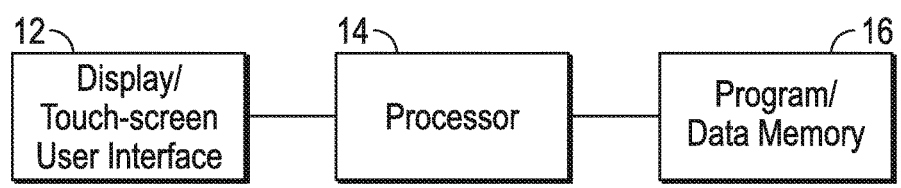
FIG. 1B is a simplified block diagram of the computing device of FIG. 1A.

Described herein are various gestures that may be used in creating and editing molecular structures that are rendered as a two or three dimensional structure on a display. The gestures may be performed on a touch-screen enabled device. An example of such a device is taught by Hotelling et al. U.S. Pat. No. 7,663,607 for example, which is incorporated by reference herein at least for its description of the hardware associated with such devices. One of ordinary skill in the art will recognize that the device is not limited to that described in this patent, and that the method may be used with any touch-screen capable device, including smart phones, tablet computer devices, and touch screens and touch pads on laptops. Commercial embodiments of suitable touch screen enabled devices include a wide variety of smart phone and tablet computer devices such as the well known iPhone® and iPad® devices. FIG. 1A is an illustration of one such device 10, comprising a display with an overlying touch sensitive interface 12. Gestures performed by a user with their fingertips (or sometimes a stylus) by touching and sliding their fingertips on the display/touch-screen interface in response to images on the display are interpreted by the device as commands. FIG. 1B is a simplified block diagram of the electronics of the device 10. The display/touch-screen interface is coupled to a processor 14, which is itself coupled to a program/data memory 16 storing operating system and application programs. The system interprets the fingertip gestures, and performs commands which may include display updates in response to the interpretations of the gestures. In this system, the touch screen user interface is located over the display, but a separate touch screen interface from the display can be used as well. Thus, the display/touch-screen user interface 12 of FIG. 1B may be a combined display with a touch sensitive sheet overlaid thereon, or display separate from a touch screen user interface such as a device with an LCD display and a separate touch pad.

The various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product. In some advantageous implementations, computer instructions that cause a touch screen enable device to perform the methods herein described are stored as an "app" on a server that is accessible to the touch screen enabled device over a computer network such as the Internet. The instructions can be downloaded to the touch screen enabled device and stored on a computer readable electronic memory in the touch screen enabled device.

Traditional chemical drawing programs are template centric applications. Complex chemical structure drawings are built up through selecting templates from multiple menus and connecting templates via bonds and atoms. A more facile drawing approach, described herein, relies on a "shorthand" method for creating fast chemical drawing where the user remains on the drawing surface without the need for "hunting and pecking" through menus. The gestures described are designed to simplify the drawing process through "short-cut gestures" to quickly build complicated structures. The simplified gestures obviate the need for multiple template menus or drawing each atom by hand. Publication ready drawings are created without drawing accuracy on the screen. The location of the gesture is ignored, and the size of the gesture does not matter to the recognition of the gesture. This method works equally well for a touch screen device as well as a mouse.

Figure 2A:
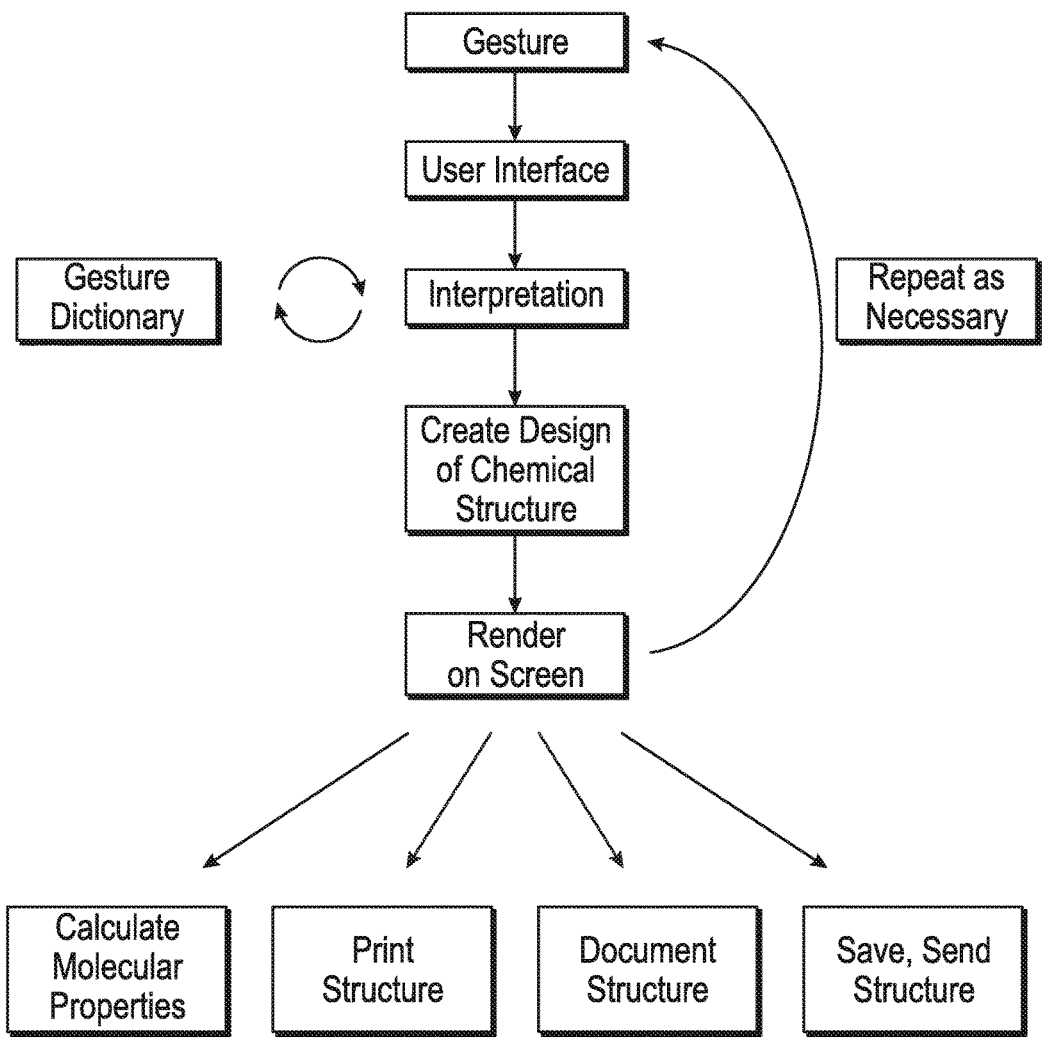
FIG. 2A is a flow chart for new molecule generation.

Referring now to FIG. 2A, this simplified flow chart shows a computer application implementing a gesture in accordance with some embodiments of the present invention for creating a new molecule. The process begins with a gesture that may include placing the hand parts down on the multi-touch surface and interaction occurs with the user interface. The machine interprets the gesture by referring to the gesture dictionary, and the machine creates the design of the chemical structure, followed by rendering the structure on the screen. This process is repeated until a desired structure has been completed. Once the structure is completed, then the typical actions include calculating molecular properties, printing the structure, documenting the structure as well as saving and sending the structure.

Figure 2B:
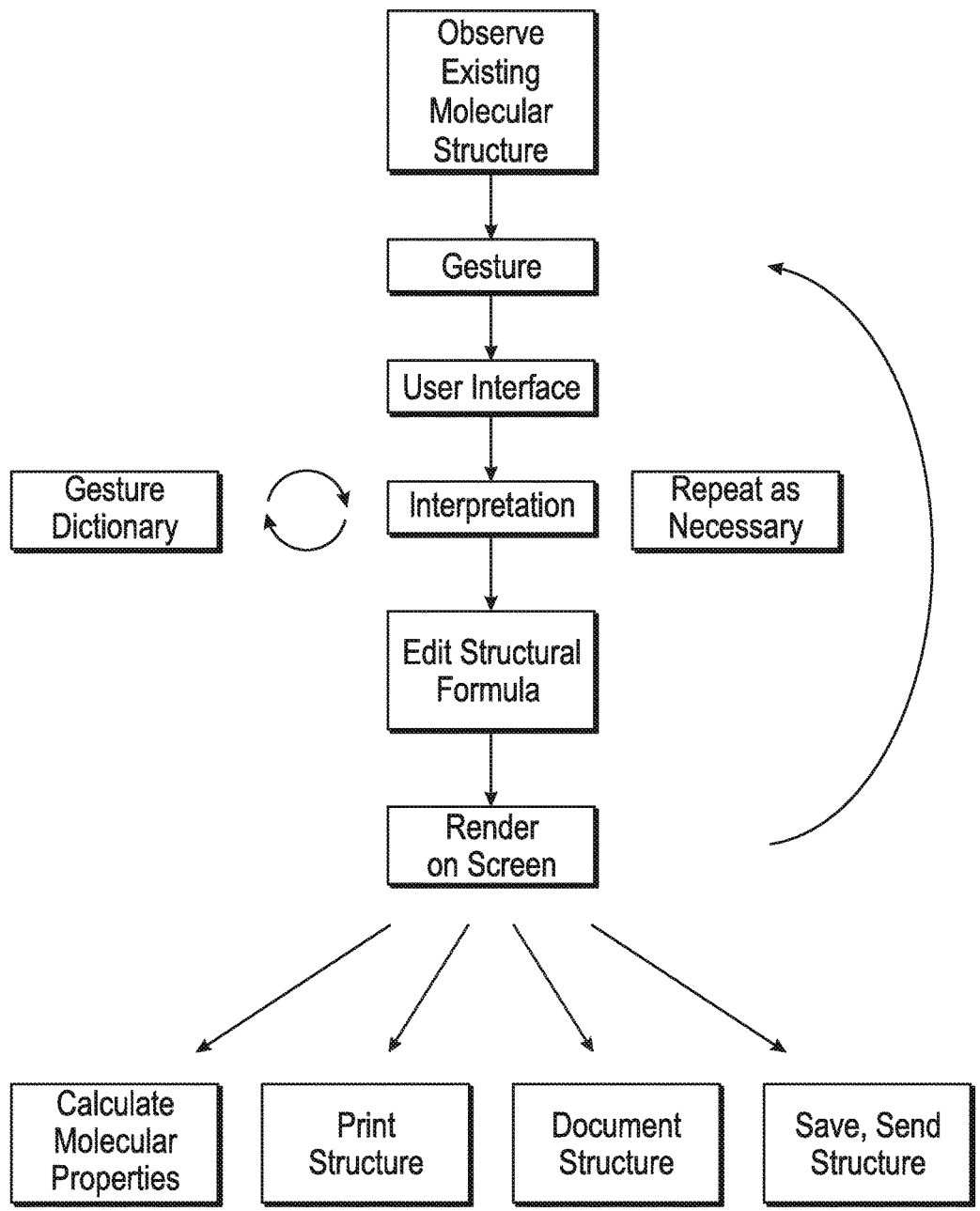
FIG. 2B is a flow chart for editing molecular structures.

Set forth below in FIG. 2B is a simplified flow chart of a computer application implementing a gesture in accordance with some embodiments of the present invention for editing a previously drawn molecule. The process begins with observing an existing molecular structure followed by placing the hand parts down on the multi-touch surface and interaction occurs with the user interface. The machine interprets the gesture by referring to the gesture dictionary, and the machine edits the design of the chemical structure, followed by rendering the structure on the screen. This process is repeated until desired structure has been completed. Once the structure is completed, then the typical actions include calculating molecular properties of the structure, printing the structure, documenting the structure as well as saving and sending the structure.

Definitions of Some Additional Gestures:

Tap: Tap the touch screen with one or more fingers.

Double tap: Tap the touch screen twice with one or more fingers. The second tap must occur within a defined time period.

Touch and hold (also known as long press): Touch the screen with one or more fingers for a specified amount of time, but leave the fingers in contact with the screen.

Drag (also known as pan): Slide one or more fingers across the screen while in contact with the screen, generally initiated with a stationary touch, followed by relatively slow motion over the screen surface in straight or curved trajectories, and with the motion stopping while the finger(s) are still in contact with the screen.

Swipe: A swipe is a slide of one or more fingers across the screen in an approximately straight line in any direction, generally performed with a "throwing"-like gesture where the finger(s) are in motion as they contact and leave the screen.

Two fingered swipe: A two fingered swipe is a swipe as described above with two fingers simultaneously in contact with the screen, generally in close proximity to each other and initiating and terminating contact with the screen at substantially the same time.

Pinch: Slide two or more fingers across the screen while in contact with the screen. Can be a pinch where the fingers are coming together or where the fingers are being moved apart One fingered circle: Trace a circle clockwise or counter-clockwise with one finger on the screen.

Two fingered circle: Trace a circle clockwise or counter-clockwise with two fingers on the screen.

Two fingered rotation: Two fingers held apart rotate in a circular fashion clockwise or counterclockwise around a pivot point on the screen.

Checkmark: Trace a checkmark figure with one or more fingers on the screen.

Inverted Checkmark: Trace an inverted checkmark figure with one or more fingers on the screen.

From the gestures described above, at least the one fingered circle, the two fingered circle and the checkmark and the inverted checkmark gestures are unique and original gestures never seen or described before for any chemistry drawing application. The new gestures are added to gesture dictionary provided by Apple.

In addition to the above gestures, various gestures are possible for creating and editing a chemical structure. These gestures include spread-hand and neutral detection taught in Westerman et al., U.S. Pat. No. 7,705,830. The gestures also include the pinch, rotate and tap gestures including gesture/translation/liftoff operations described in Westerman et al. in U.S. Patent Application Publication 2008/0309632.

The following table describes examples of operations on the 2 dimensional and 3-dimensional molecular structures, gestures used to cause the operation, and the machine response to the gestures. These unique gestures are derived from the natural manner in which scientists draw structures using pen and paper so that the gesture would be natural and easy to remember by the scientist. The gestures are a facile short-hand method for drawing chemical structures. Additionally, the gesture are easy to complete, and simple for the system to recognize and interpret. From Table 1, at least the following gestures have never been described or used for editing and creating chemical structures: the two fingered rotation to cause rotation and the two fingered pinch to afford scaling. For the rest of the gestures described in Table 1, similar manipulations using a mouse have been used, but it has never been described where the machine is responding to a touch gesture. These gestures and the combination of multiple gestures in combinations provide a more facile method for creating and editing molecular structures than previously known before using a mouse, thereby enhancing productivity. Performing these functions with touch gestures is an especially advantageous use of touch screen technology that has not before been contemplated.

TABLE 1

Operations on 2-Dimensional and 3-Dimensional Molecular Structures

| Operation | Gesture | Machine Response |
|---|---|---|
| Atom, Functional Group, or Bond Selection | Single tap | Interprets gesture as selection gesture, retrieves commands for operation and executes desired atom, functional group, or bond selection, with visualization on display screen. |
| Molecule Selection | Double tap | Interprets gesture as selection gesture, retrieves commands for operation and executes desired molecule selection, with visualization on display screen. |
| Rotation | Two fingered rotation | Interprets gesture as rotation gesture, retrieves commands for operation and executes desired rotation movement, with visualization on display screen. |
| Molecule or Atom Translation | One fingered drag | Interprets gesture as translation gesture, retrieves commands for operation and executes desired translation movement, with visualization on display screen. |
| Scaling | Two fingered pinch | Interprets gesture as pinch gesture, retrieve commands for operations and executes desired scaling movement, with visualization on display screen. |
| Return to Default Scaling | Two fingered double tap | Interprets gesture as two fingered double tap, retrieve commands for operations and executes desired scaling movement to return to the default size settings, with visualization on display screen. |

The following describes operations on the 2-dimensional and 3-dimensional molecular structures, followed by the gestures that can be used to control the changes. As will be described below, the system may have different user selectable modes, where in some cases identical gestures can result in different responses depending on the mode selected when the gesture is performed.

Figure 3:
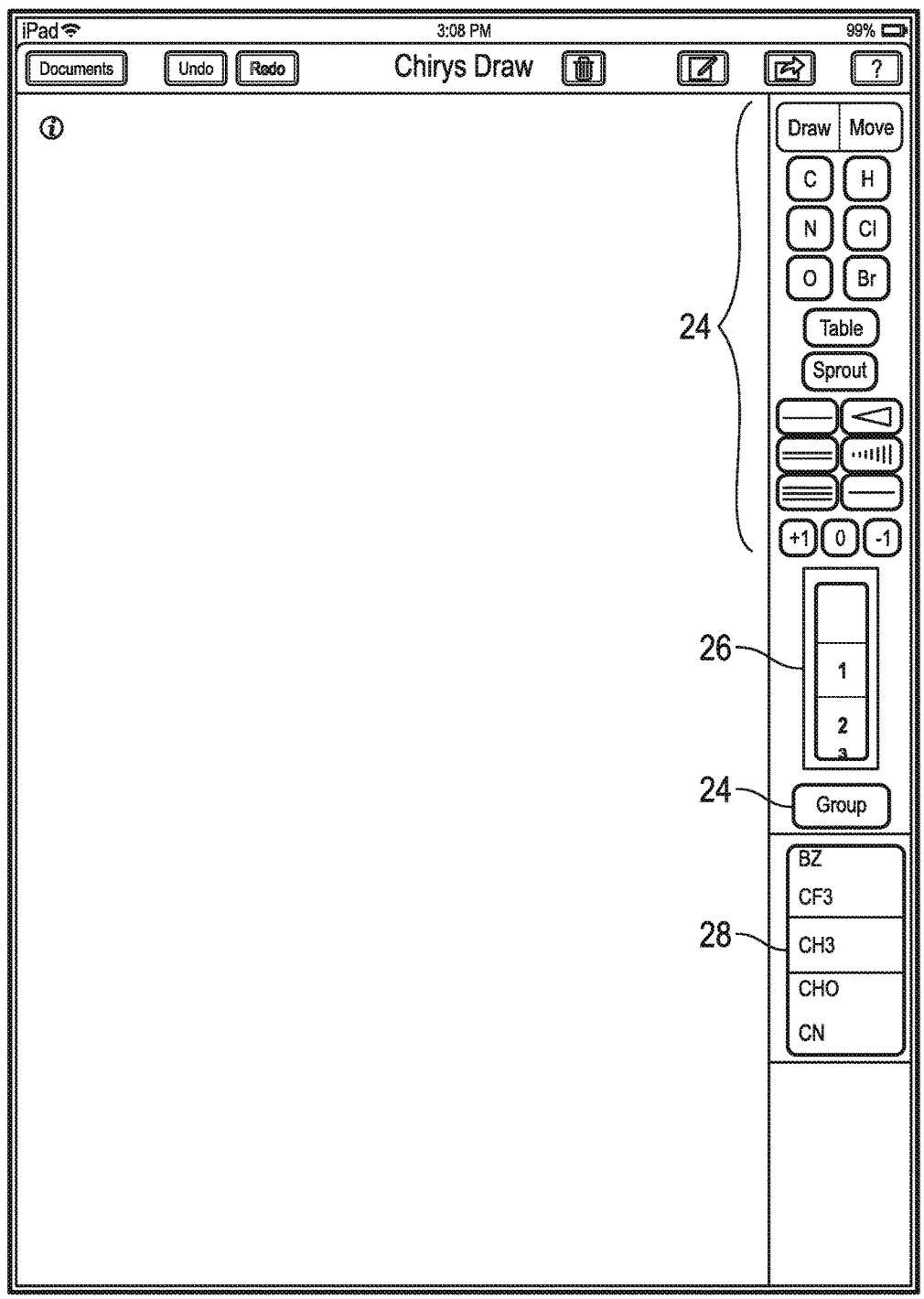
FIG. 3 shows the blank, full drawing surface.

As seen in FIG. 3, one implementation of a graphical user interface for creating and/or manipulating symbols representing chemical structures is shown for the drawing surface. The graphical user interface may, for example, be presented to a user on the display 12 of FIG. 1A. The graphical user interface includes buttons 24, a number wheel 26, and a chemical group wheel 28. The buttons are provided in a manner conventional in the touch screen user interface field as locations where a tap on the screen produces a function performed by the device, where the function may be a change to the content of the images displayed to the user. The number wheel 26 and group wheel 28 function in a conventional manner, where a user can "spin" the wheel with a swipe or drag to designate a selection. In subsequent figures, the full drawing surface may be truncated in order to save space.

Selection, Rotation, Translation, Scaling in 2 and 3-Dimensions:

Selection of one atom, functional group, or bond can be selected by operating the touch-screen with a particular gesture. As described in Table 1, a suitable gesture used for atom, functional group, or bond selection is a one fingered tap.

Figure 4:
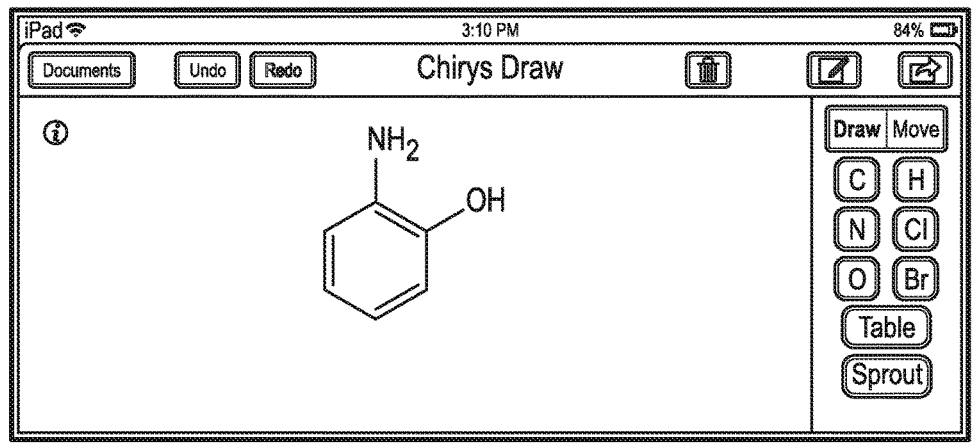
FIG. 4 shows the before and after screen shots of selecting an atom.
Figure 4:
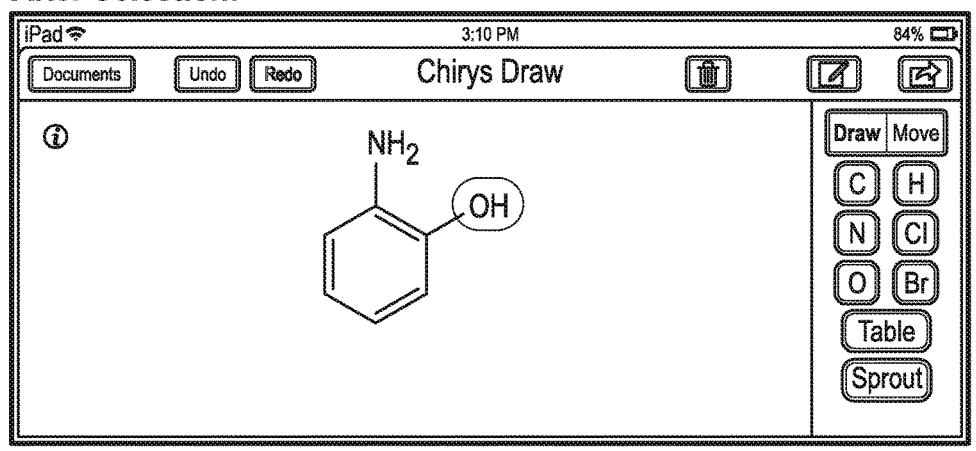

Referring now to FIG. 4, selection of one atom, functional group, or bond in the context of one or more atoms, bonds, or molecules may be accomplished by operating the touch-screen with a particular gesture, a single tap. The molecules may be selected in relation to any part of the overall system. The machine then interprets the gesture as an atom, a functional group, or a bond selection, retrieves the commands for the operation from the Gesture Dictionary from the Gesture Dictionary, and then executes the desired selection, as visualized on the display screen.

It is especially advantageous to combine the selection gesture and response as follows. Selection of an atom, a functional group, or a bond can be accomplished by operating the touch-screen with a particular gesture. The typical gesture used for atom, functional group, or bond selection is a one fingered tap. Selection of one atom, functional group, or bond in the context of one or more entire molecules may be accomplished by operating the touch-screen with a particular gesture, a single tap. The molecules may be selected in relation to any part of the overall system. The machine then interprets the gesture as an atom, a functional group, or a bond selection, retrieves the commands for the operation from the Gesture Dictionary, and then executes the desired selection, as visualized on the display screen. The selected atom or bond is then observed to have been highlighted in relation to any part of the overall system.

Selection of one molecule can be accomplished by operating the touch-screen with a particular gesture. As described in Table 1, a suitable gesture used for molecule selection is a one fingered double tap on an atom, functional group, or bond contained in the molecule.

Figure 5:
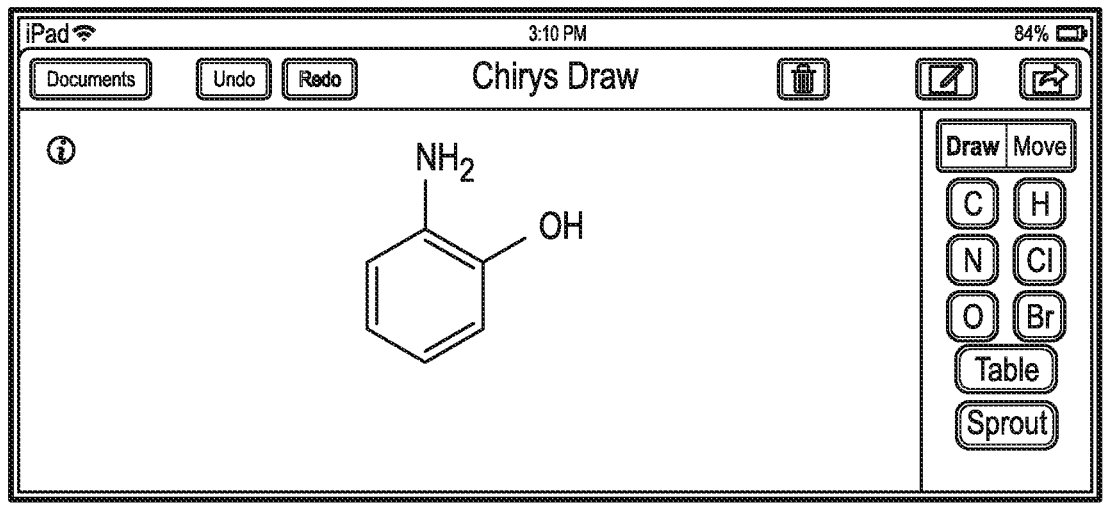
FIG. 5 shows the before and after screen shots of selecting a molecule.
Figure 5:
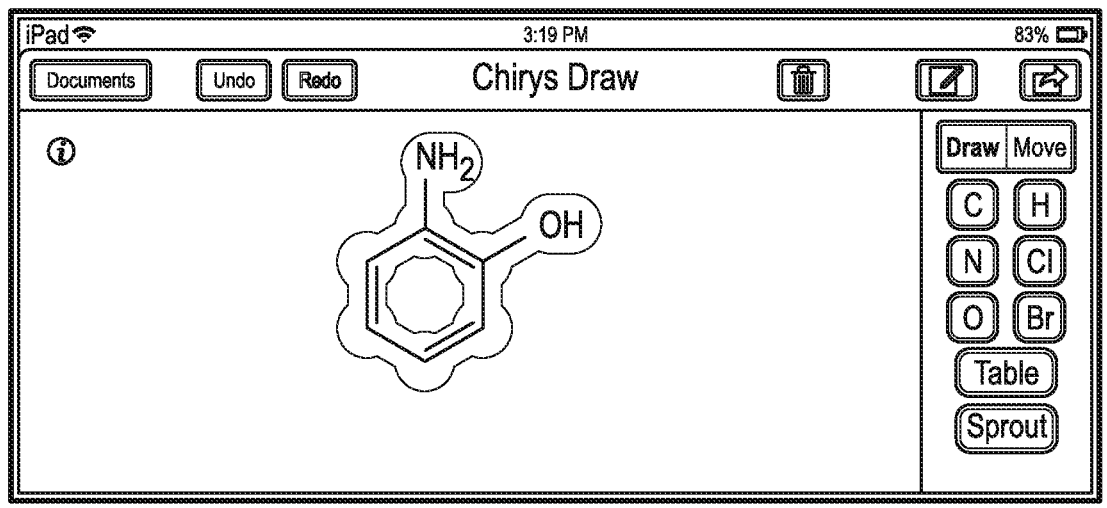

As seen in FIG. 5, selection of one molecule in the context of other molecules may be accomplished by operating the touch-screen with a particular gesture, a one fingered double tap. The molecule may be selected in relation to any part of the overall system. The machine then interprets the gesture as a selection, retrieves the commands for the operation from the Gesture Dictionary, and then executes the selection, as visualized on the display screen.

It is especially advantageous to combine the selection gesture and response as follows. Selection of one molecule can be accomplished by operating the touch-screen with a particular gesture. A suitable gesture used for molecule selection is a one fingered double tap on an atom, a functional group, or a bond contained in the molecule. Selection of one molecule in the context of other molecules may be accomplished by operating the touch-screen with a particular gesture, a one fingered double tap. The molecule may be selected in relation to any part of the overall system. The machine then interprets the gesture as a selection, retrieves the commands for the operation from the Gesture Dictionary, and then executes the selection, as visualized on the display screen. The selected molecule is then observed to have been highlighted in relation to any other parts of the overall system.

Rotation in any axis a system of one or more molecules as a complete system may be accomplished by operating the touch-screen with a particular gesture. As described in Table 1, a suitable gesture used for rotation is a two fingered rotation, where both fingers, held apart, move in a circular fashion in either a clockwise or counterclockwise direction around a pivot point on the screen. Even if the fingers are held together, the device can detect two distinct touches by each individual finger.

Figure 6:
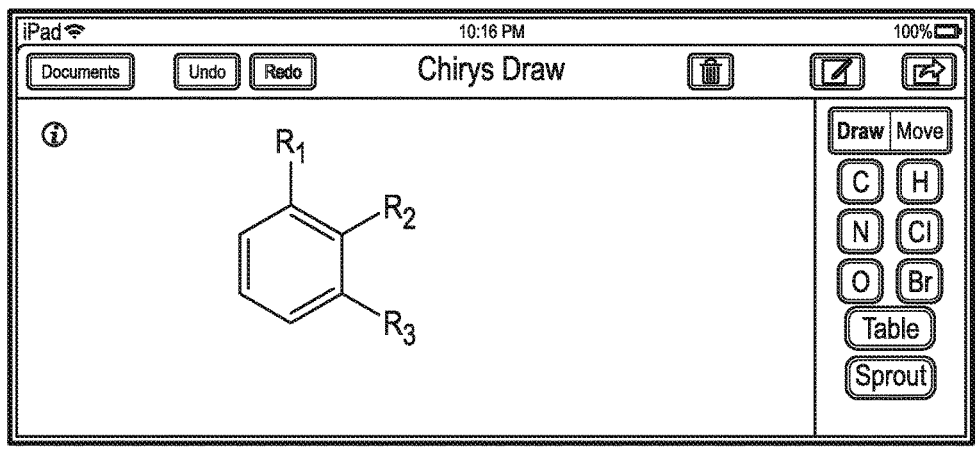
FIG. 6 shows the before and after view of rotating a selected molecule.
Figure 6:
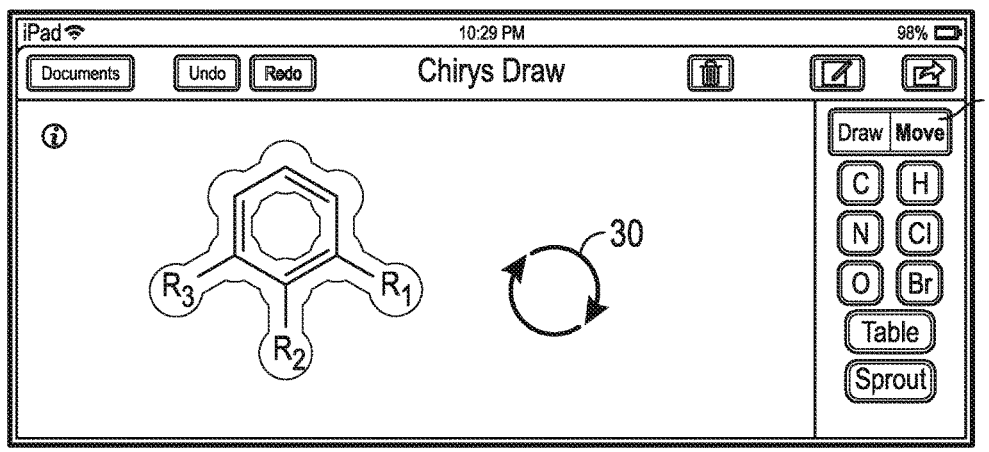

In FIG. 6, rotating in any axis one or more molecules in the context of one or more molecules may be accomplished by operating the touch-screen with a particular gesture, a two fingered rotation. The molecules may be rotated in relation to any part of the overall system. First, a "Move Mode" may be chosen by a user. Choosing a "Move Mode" may be accomplished by operating the touch-screen with a particular gesture, such as tapping on a particular icon 22, "Move", on the display. The molecule(s) to be moved are then selected (e.g. with a double tap as described above), or otherwise denoted as the moving objects, and then the gesture may be the same as rotation gesture described above, shown in FIG. 6 as the two arrows 30, where a user's fingers are initially placed at start of each arrow and move as shown by the arrow trajectories. The machine then interprets the gesture as a rotation, retrieves the commands for the operation from the Gesture Dictionary, and then executes the desired movement, as visualized on the display screen.

It is especially advantageous to combine the rotation gesture and response as follows. Rotation in any axis a system of one or more molecules as a complete system may be accomplished by operating the touch-screen with a particular gesture. A suitable gesture used for rotation is a two fingered rotation, where both fingers move in a circular fashion in either a clockwise or counterclockwise direction. The molecules may be rotated in relation to any part of the overall system. First, a "Move Mode" may be chosen by a user. Choosing a "Move Mode" may be accomplished by operating the touch-screen with a particular gesture, such as tapping on a particular icon, "Move", on the display. The molecule(s) to be moved are then selected (e.g. with a double tap as described above), or otherwise denoted as the moving objects, and then the gesture may be the same as rotation gesture described above. The machine then interprets the gesture as a rotation, retrieves the commands for the operation from the Gesture Dictionary, and then executes the desired movement, as visualized on the display screen. The selected molecule(s) is then observed to have been rotated in relation to any other parts of the overall system.

Translation in any direction of a system of one or more molecules as a complete system may be accomplished by operating the touch-screen with a particular gesture. As described in Table 1, a suitable gesture used for translation is a one fingered drag across the screen.

Figure 7:
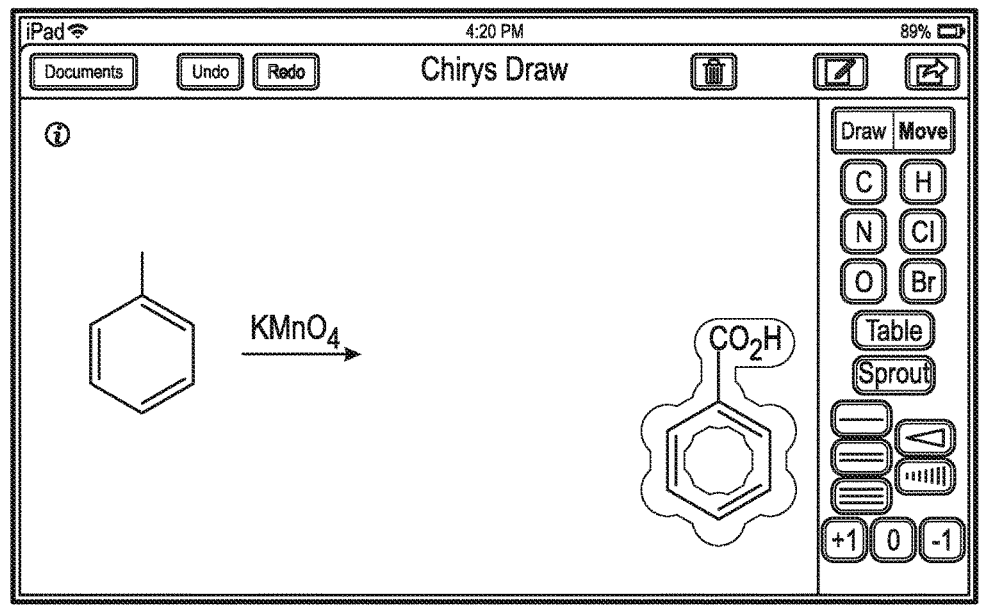
FIG. 7 shows the before and after screen shots of translating a molecule.
Figure 7:
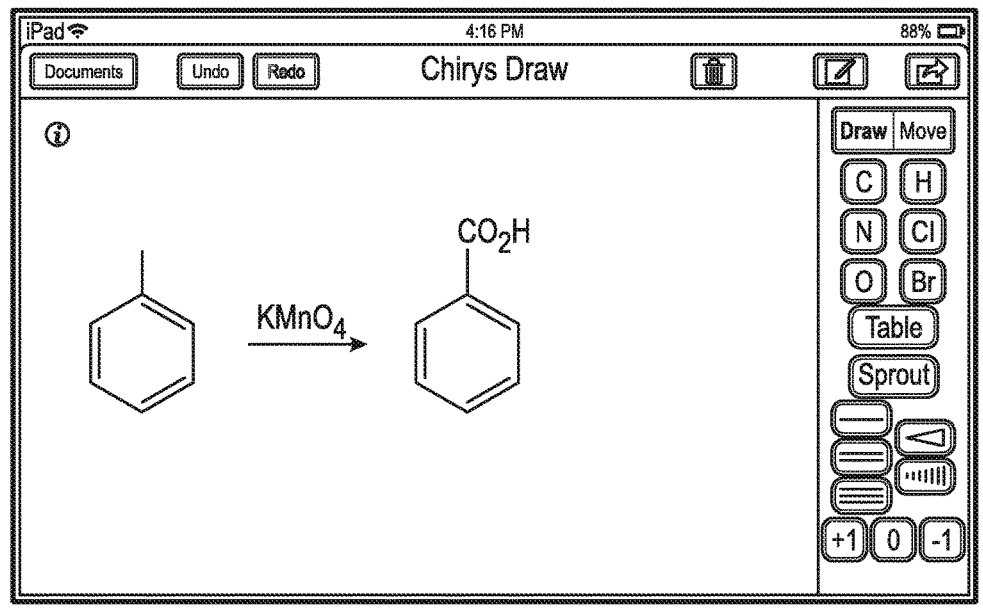

As seen in FIG. 7, translating in any direction one or more molecules in the context of one or more molecules may be accomplished by operating the touch-screen with a particular gesture. First, a "Move Mode" may be chosen by a user. Choosing a "Move Mode" may be accomplished by operating the touch-screen with a particular gesture, such as tapping on a particular icon, "Move", on the display. The molecule(s) to be moved are first selected (e.g. with a double tap as described above), or otherwise denoted as the moving objects, and then the gesture may be the same as the translation gesture above, a one fingered drag. The machine then interprets the gesture as a translation, retrieves the commands for the operation from the Gesture Dictionary, and then executes the desired movement, as visualized on the display screen.

It is especially advantageous to combine the molecule translation gesture and response as follows. Translation in any direction a system of one or more molecules as a complete system may be accomplished by operating the touch-screen with a particular gesture. The typical gesture used for translation is a one fingered drag across the screen. First, a "Move Mode" may be chosen by a user. Choosing a "Move Mode" may be accomplished by operating the touch-screen with a particular gesture, such as tapping on a particular icon, "Move", on the display. The molecule(s) to be moved are first selected (e.g. with a double tap as described above), or otherwise denoted as the moving objects, and then the gesture may be the same as the translation gesture above, a one fingered drag. The machine then interprets the gesture as a translation, retrieves the commands for the operation from the Gesture Dictionary, and then executes the desired movement, as visualized on the display screen. The selected molecule(s) is then observed to have been translated in relation to one or more other parts of the overall system.

Translation in any direction a system of one or more atoms such as a functional group portion of a molecule as a unit may be accomplished by operating the touch-screen with a particular gesture. A suitable gesture used for translation is a one fingered drag across the screen.

Figure 8:
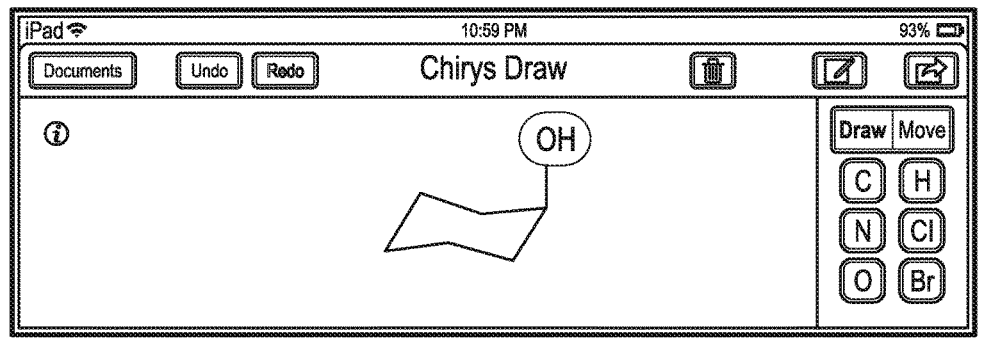
FIG. 8 shows the before and after screen shots of translating an atom.
Figure 8:
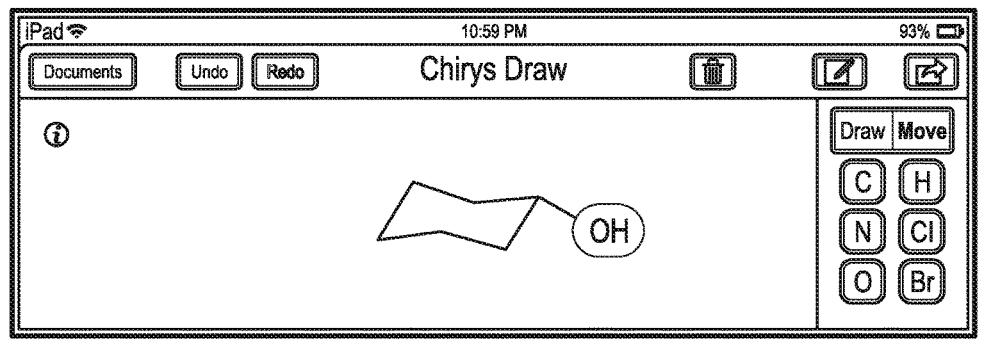

As seen in FIG. 8, translating in any direction one or more atoms in the context of one or more atoms may be accomplished by operating the touch-screen with a particular gesture. First, a "Move Mode" may be chosen by a user. Choosing a "Move Mode" may be accomplished by operating the touch-screen with a particular gesture, such as tapping on a particular icon, "Move", on the display. The atom(s) to be moved are first selected (e.g. with a single tap as described above), or otherwise denoted as the moving objects, and then the gesture may be the same as the translation gesture above, a one fingered drag. The machine then interprets the gesture as a translation, retrieves the commands for the operation from the Gesture Dictionary, and then executes the desired movement, as visualized on the display screen.

It is especially advantageous to combine the one or more atom translation gesture and response as follows. Translating in any direction one or more atoms in the context of one or more atoms may be accomplished by operating the touch-screen with a particular gesture. First, a "Move Mode" may be chosen by a user. Choosing a "Move Mode" may be accomplished by operating the touch-screen with a particular gesture, such as tapping on a particular icon, "Move", on the display. The atom(s) to be moved are first selected (e.g. with a single tap as described above), or otherwise denoted as the moving objects, and then the gesture may be the same as the translation gesture above, a one fingered drag. The machine then interprets the gesture as a translation, retrieves the commands for the operation from the Gesture Dictionary, and then executes the desired movement, as visualized on the display screen. The selected atom(s) is then observed to have been translated in relation to any part of the overall system.

Scaling to the original default scaling of one or more molecules may be accomplished by operating the touch-screen with a particular gesture. As described in Table 1, a suitable gesture used for scaling to default settings is a two fingered double tap.

Figure 9:
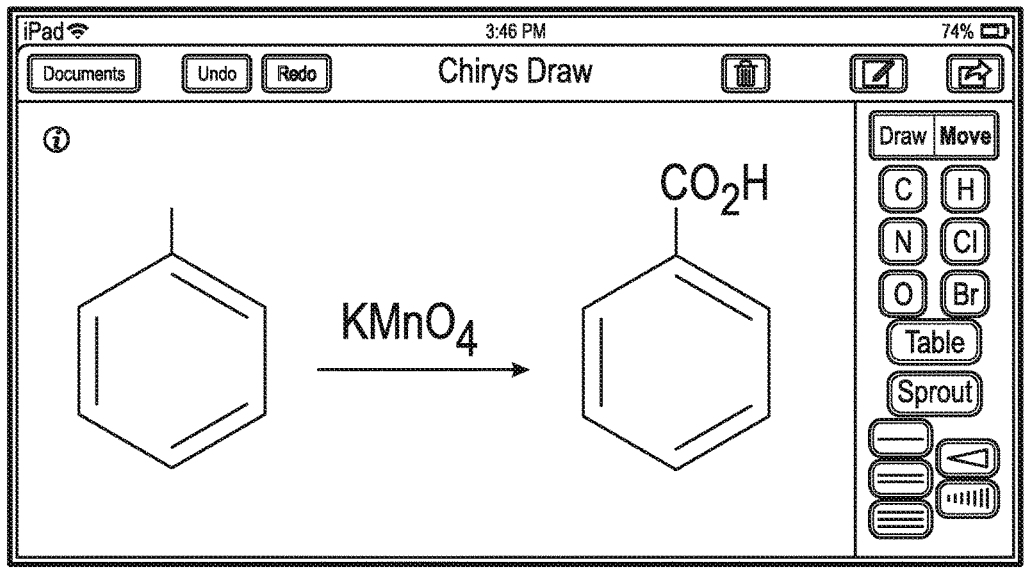
FIG. 9 shows the before and after screen shots of scaling a molecular drawing.
Figure 9:
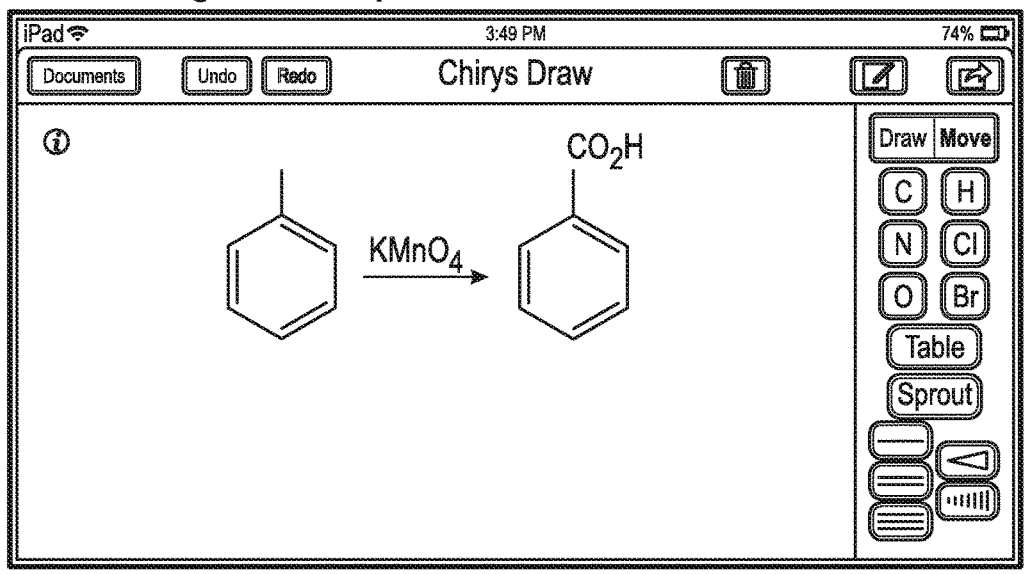

As can be seen in FIG. 9, scaling of one or more molecules to the original default scaling may be accomplished by operating the touch-screen with a particular gesture, a two fingered double tap. The molecules may be scaled in relation to any part of the overall system. First, a "Move Mode" may be chosen by a user. Choosing a "Move Mode" may be accomplished by operating the touch-screen with a particular gesture, such as tapping on a particular icon, "Move", on the display. No drawn object needs to be selected, and then the gesture may be the same as scaled described above. The machine then interprets the gesture as a scaling to default scaling, retrieves the commands for the operation from the Gesture Dictionary, and then executes the desired scaling, as visualized on the display screen to the default scaling settings.

It is especially advantageous to combine the return to default scaling gesture and response as follows. Scaling to the original default scaling of one or more molecules may be accomplished by operating the touch-screen with a particular gesture. A suitable gesture used for scaling to default settings is a two fingered double tap. Scaling of one or more molecules to the original default scaling may be accomplished by operating the touch-screen with a particular gesture, a two fingered double tap. The molecules may be scaled in relation to any part of the overall system. First, a "Move Mode" may be chosen by a user. Choosing a "Move Mode" may be accomplished by operating the touch-screen with a particular gesture, such as tapping on a particular icon, "Move", on the display. No drawn object needs to be selected, and then the gesture may be the same as scaled described above. The machine then interprets the gesture as a scaling to default scaling, retrieves the commands for the operation from the Gesture Dictionary, and then executes the desired scaling, as visualized on the display screen to the default scaling settings. The selected molecule(s) is then observed to have been scaled to default settings in relation to any part of the overall system.

Creating and Editing Molecular Structures in 2 and 3-Dimensions:

Creating and editing molecular structures may be accomplished by operating the touch-screen with a particular gesture. Performing these functions with touch gestures is an especially advantageous use of touch screen technology that has not before been contemplated. Creating and editing of molecular structures on a touch-screen may include many of the creating and editing operations previously performed using a mouse or a keyboard. These operations include those disclosed by Facci et al. in U.S. Pat. No. 5,461,580. One of ordinary skill in the art will appreciate that the creating and editing operations, however, are not limited to those described in this patent. Some creating and editing operations that may be performed using the touch-screen will now be described.

The following table describes the edits on the 2-dimensional and 3-dimensional molecular structures, gestures used to cause the operation, and the machine response from the gestures. From Table 2, at least the following gestures have never been described or used for editing and creating chemical structures: the single or double fingered circle to provide saturated and unsaturated rings, the one fingered swipe to give a carbon chain of specific length, the appending a gem-dimethyl group by a checkmark gesture, the single fingered swipe that produces a group alignment, the two-fingered swipe to give cis-trans isomerization of alkene bonds, a one-fingered swipe to give a reaction arrow and a two-fingered swipe to produce a retrosynthetic arrow. For the rest of the gestures described in Table 2, manipulations using a mouse have been used, but it has never been described where the machine is responding to a touch gesture. These gestures and the combination of multiple gestures in combinations provide a more facile method for creating and editing molecular structures than previously known, thereby enhancing productivity. Performing these functions with touch gestures is an especially advantageous use of touch screen technology that has not before been contemplated.

TABLE 2

Edits on 2-Dimensional and 3-Dimensional Molecular Structures

| Operation | Gesture | Machine Response |
|---|---|---|
| Drawing or appending a saturated ring | Single fingered circle in either a clockwise or counterclockwise direction | Interprets gesture as single fingered circle gesture, retrieves commands for operation and executes desired saturated ring generation movement, with visualization on display screen. |
| Drawing or appending an unsaturated ring | Two fingered circle in either a clockwise or counterclockwise direction | Interprets gesture as two fingered circle gesture, retrieves commands for operation and executes desired unsaturated ring generation movement, with visualization on display screen. |
| Drawing or appending a saturated chain | One fingered swipe | Interprets gesture as swipe gesture, retrieves commands for operation and executes desired saturated chain generation movement, with visualization on display screen. |
| Append (Sprout) Methyl Group | One fingered tap on selected atom followed by selection of "Sprout" button | Interprets gesture as one fingered tap gesture, retrieves commands for operation and executes desired append a methyl group selection, with visualization on display screen. |
| Append gem-Dimethyl Group | One fingered tap on selected atom followed by single fingered check mark | Interprets gesture as single fingered checkmark gesture on modifier button, retrieve commands for operations and executes desired gem-dimethyl generation movement, with visualization on display screen. |
| Creating ring closure from two selected atoms | Sequential one fingered tap on two selected atoms followed by one fingered tap of "bond" button | Sequentially interprets gesture as one fingered tap gesture followed by another one fingered tap gesture, retrieves commands for operation and executes desired ring closure, with visualization on display screen. |
| Creating an intermolecular bond from two selected atoms from two distinct molecules | Sequential one fingered tap on two selected atoms followed by one fingered tap of "bond" button | Sequentially interprets gesture as one fingered tap gesture followed by another one fingered tap gesture, retrieves commands for operation and executes desired ring closure, with visualization on display screen. |
| Change Bond Order | One Fingered tap | Interprets gesture as one fingered tap gesture on modifier button, retrieves commands for operation and executes desired change bond order selection, with visualization on display screen. |
| Change stereochemistry bond perspective | One Fingered tap | Interprets gesture as one fingered tap gesture on modifier button, retrieves commands for operation and executes desired change stereochemistry bond perspective selection, with visualization on display screen. |
| Group Align | Two fingered swipe | Interprets gesture as two fingered swipe, retrieve commands for operations and executes desired alignment right or left, with visualization on display screen. |
| Cis/Trans Isomerization | Two fingered swipe | Interprets gesture as two fingered swipe, retrieve commands for operations and executes the desired cis-trans isomerization, with visualization on display screen. |
| Change Element selection | One Fingered tap | Interprets gesture as one fingered tap gesture on an element button, retrieves commands for operation and executes desired change element selection, with visualization on display screen. |
| Add/Change Formal Charge | One Fingered tap | Interprets gesture as one fingered tap gesture on a formal charge button, retrieves commands for operation and executes desired formal charge modification, with visualization on display screen. |
| Add/Change Group Abbreviation | One Fingered tap | Interprets gesture as one fingered tap gesture on Group abbreviation wheel, retrieves commands for operation and executes desired add/change group selection, with visualization on display screen. |
| Reaction Arrow Generation | One Fingered Swipe | Interprets gesture as single fingered swipe gesture, retrieves commands for operation and executes desired reaction arrow generation, with visualization on display screen. |
| Retrosynthetic Arrow Generation | Two fingered swipe | Interprets gesture as two fingered swipe, retrieve commands for operations and executes desired retrosynthetic arrow generation with visualization on display screen. |

The following describes creating and editing 2-dimensional and 3-dimensional molecular structures, followed by the gestures that can be used to control the changes.

Creating a saturated ring may be accomplished by operating the touch-screen with a particular gesture. As described in Table 2, a suitable gesture used for creating a saturated ring is tracing a circle with a single finger in either a clockwise or counterclockwise direction.

Figure 10:
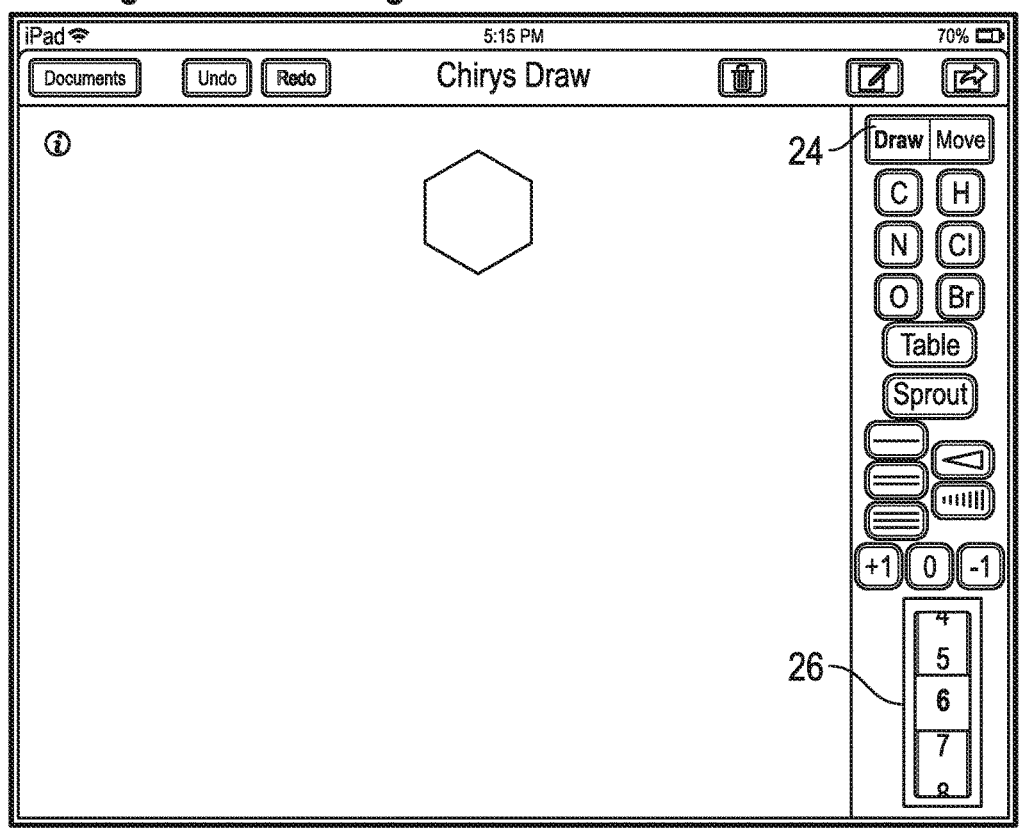
FIG. 10 depicts the screen shot of drawing a saturated ring.

As seen in FIG. 10, the "Draw Mode" may first be chosen by a user. Choosing a "Draw Mode" may be accomplished by operating the touch-screen with a particular gesture, such as tapping on a particular icon 24, "Draw", on the display. A number wheel 26 may be set to the desired number of carbon atoms of the ring. Creating a saturated ring may be accomplished by operating the touch-screen with a particular gesture, a single fingered circle (which, of course, need not be drawn perfectly by the user, but need only approximate a circle). The machine then interprets the gesture as a circle, retrieves the commands for the operation from the Gesture Dictionary, and then executes the desired ring generation, as visualized on the display screen.

It is especially advantageous to combine the saturated ring formation gesture and response as follows. The typical gesture used for creating a saturated ring is tracing a circle with a single finger in either a clockwise or counterclockwise direction. Creating a saturated ring may be accomplished by operating the touch-screen with a particular gesture. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms of the ring. Creating a saturated ring may be accomplished by operating the touch-screen with a particular gesture, a single fingered circle. The machine then interprets the gesture as a circle, retrieves the commands for the operation from the Gesture Dictionary, and then executes the desired ring generation, as visualized on the display screen. A saturated ring is observed to have been drawn in relation to any part of the overall system.

Appending a saturated ring to a bond in an existing structure may be accomplished by operating the touch-screen with a particular gesture. As described in Table 2, the gesture used for appending a saturated ring is tracing a circle with a single finger in either a clockwise or counterclockwise direction as shown by arrow 32.

Figure 11:
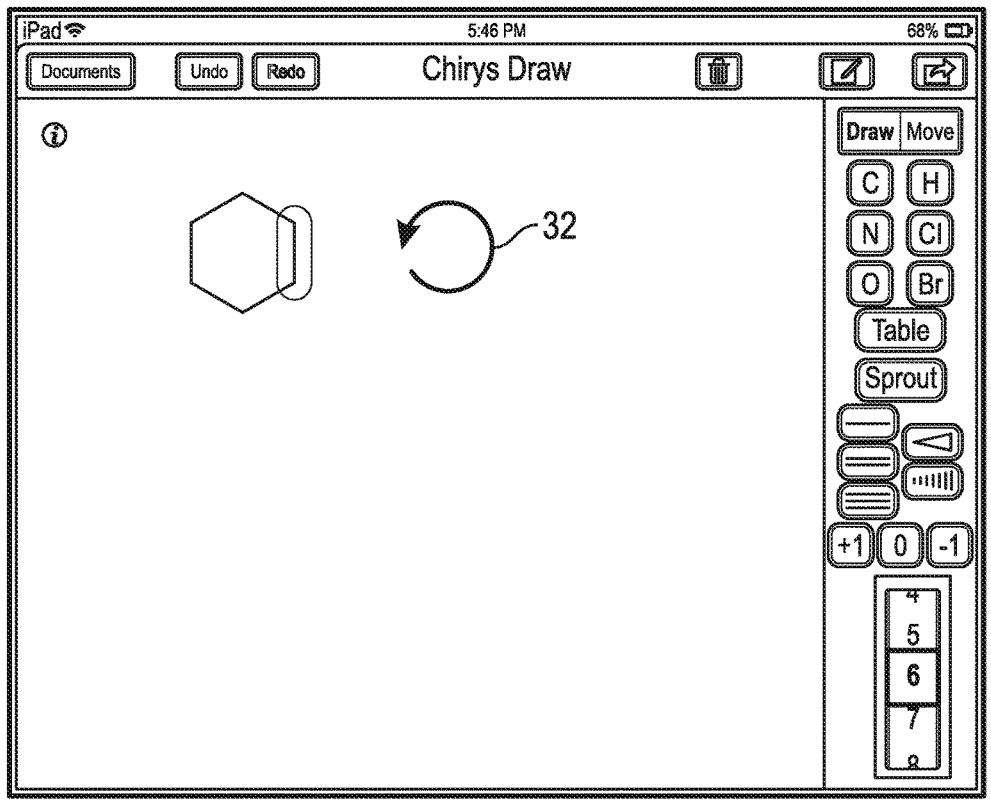
FIG. 11 shows the screen shot of appending a saturated ring.
Figure 11:
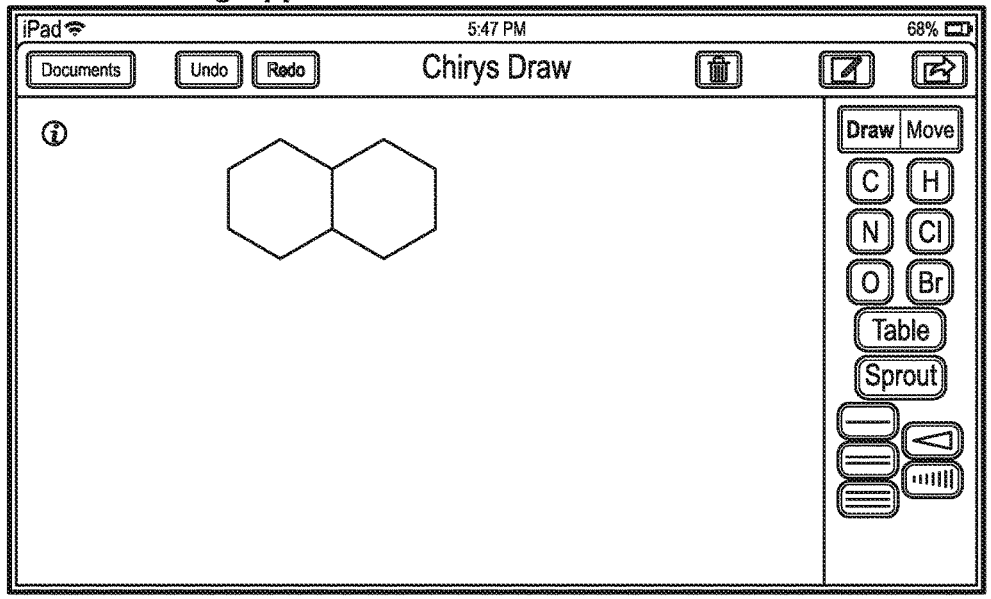

As shown in FIG. 11, the "Draw Mode" may first be chosen by a user. Choosing a "Draw Mode" may be accomplished by operating the touch-screen with a particular gesture, such as tapping on a particular icon, "Draw", on the display. The number wheel is set to the desired number of carbon atoms of the ring. Second, the bond to which the saturated ring is to be appended is selected by a single tap, as described above. Appending a saturated ring may be accomplished by operating the touch-screen with a particular gesture, drawing a single finger circle on the touch screen after the bond is selected (the same gesture as described with respect to FIG. 10, but not shown in FIG. 10). The machine then interprets the gesture as a circle, retrieves the commands for the operation from the Gesture Dictionary, and then executes the desired appending saturated ring, as visualized on the display screen.

It is especially advantageous to combine the saturated ring formation gesture and response as follows for appending a saturated ring to an existing bond. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms of the new ring. Second, the bond to which the saturated ring is to be appended is selected by a single tap. Appending a saturated ring may be accomplished by operating the touch-screen with a particular gesture, drawing a single finger circle on the touch screen. The machine then interprets the gesture as a circle, retrieves the commands for the operation from the Gesture Dictionary, and then executes the desired appending saturated ring, as visualized on the display screen. A saturated ring is observed to have been appended to an existing bond in relation to the previously drawn ring and to any other parts of the overall system.

Appending a saturated ring to an atom of a molecule to generate a spiro structure may be accomplished by operating the touch-screen with a particular gesture. As described in Table 2, a suitable gesture used for appending a saturated ring to a selected atom is tracing a circle with a single finger in either a clockwise or counterclockwise direction (the same gesture as illustrated in FIG. 11).

Figure 12:
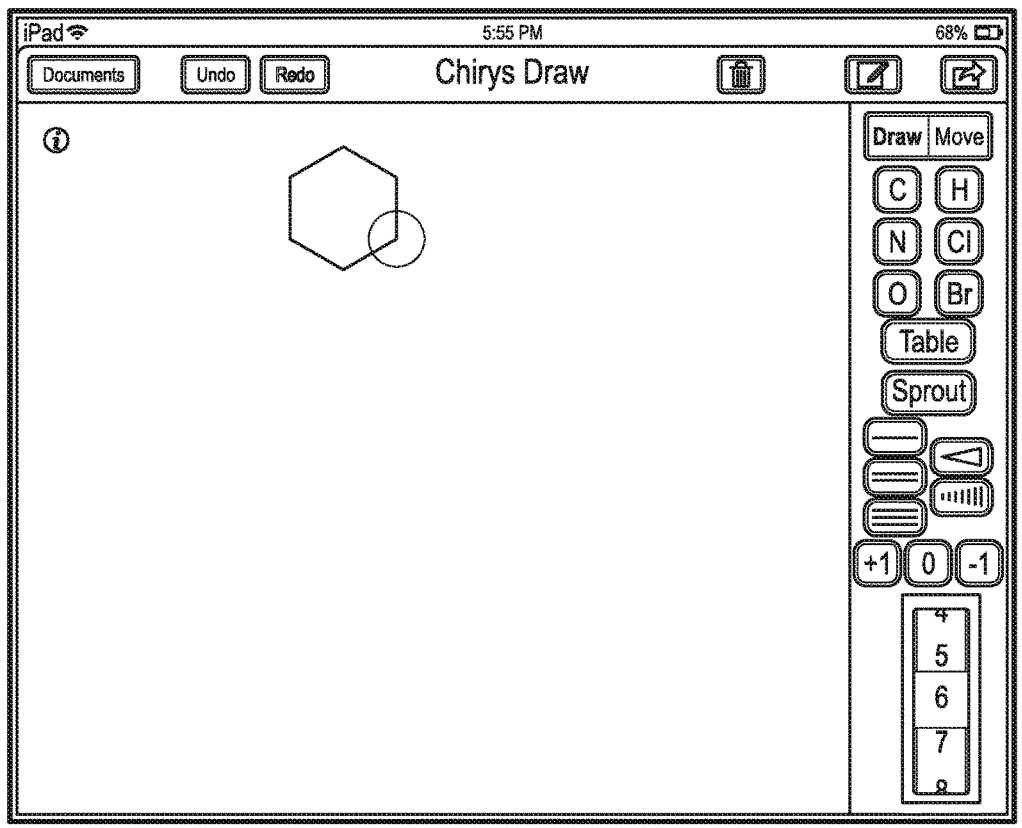
FIG. 12 shows the screen shot of appending a saturated ring to an atom of a molecule to generate a spiro structure.
Figure 12:
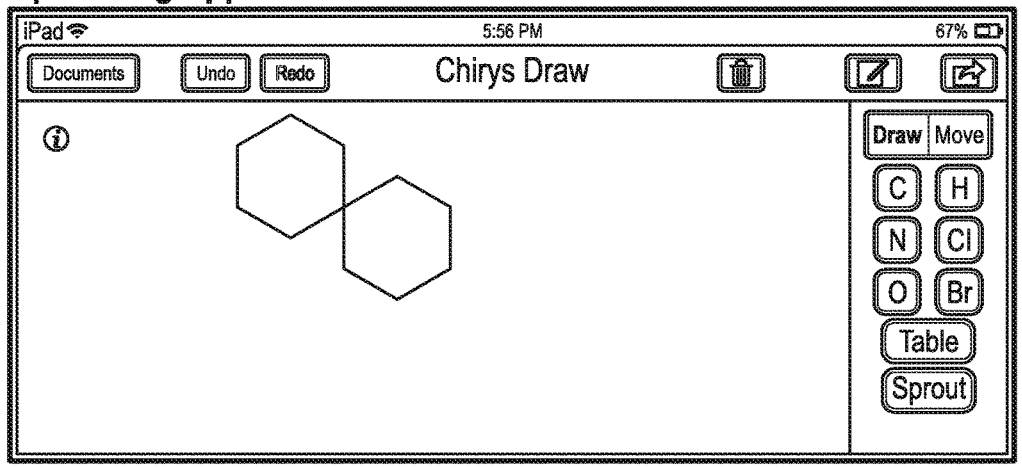

As seen in FIG. 12, the "Draw Mode" may first be chosen by a user. Choosing a "Draw Mode" may be accomplished by operating the touch-screen with a particular gesture, such as tapping on a particular icon, "Draw", on the display. The number wheel is set to the desired number of carbon atoms. Second, the atom to which the saturated ring is to be appended is selected by a single tap as described above, for example. Appending a saturated ring to an atom may be accomplished by operating the touch-screen with a particular gesture, drawing a single finger circle on the touch screen. The machine then interprets the gesture as a circle, retrieves the commands for the operation from the Gesture Dictionary, and then executes the desired appending saturated ring, as visualized on the display screen.

It is especially advantageous to combine the gesture and response to append a saturated ring as follows. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms of the new ring. Second, the atom to which the saturated ring is to be appended is selected by a single tap. Appending a saturated ring to an atom may be accomplished by operating the touch-screen with a particular gesture, drawing a single finger circle on the touch screen. The machine then interprets the gesture as a circle, retrieves the commands for the operation from the Gesture Dictionary, and then executes the desired appending saturated ring, as visualized on the display screen. A saturated ring is observed to have been appended (spiro ring generation) in relation to the previously drawn ring and to any other parts of the overall system.

Creating an unsaturated ring may be accomplished by operating the touch-screen with a particular gesture. As described in Table 2, a suitable gesture used for creating an unsaturated ring is tracing a circle (or approximation thereof as noted above) with two fingers in either a clockwise or counterclockwise direction.

Figure 13:
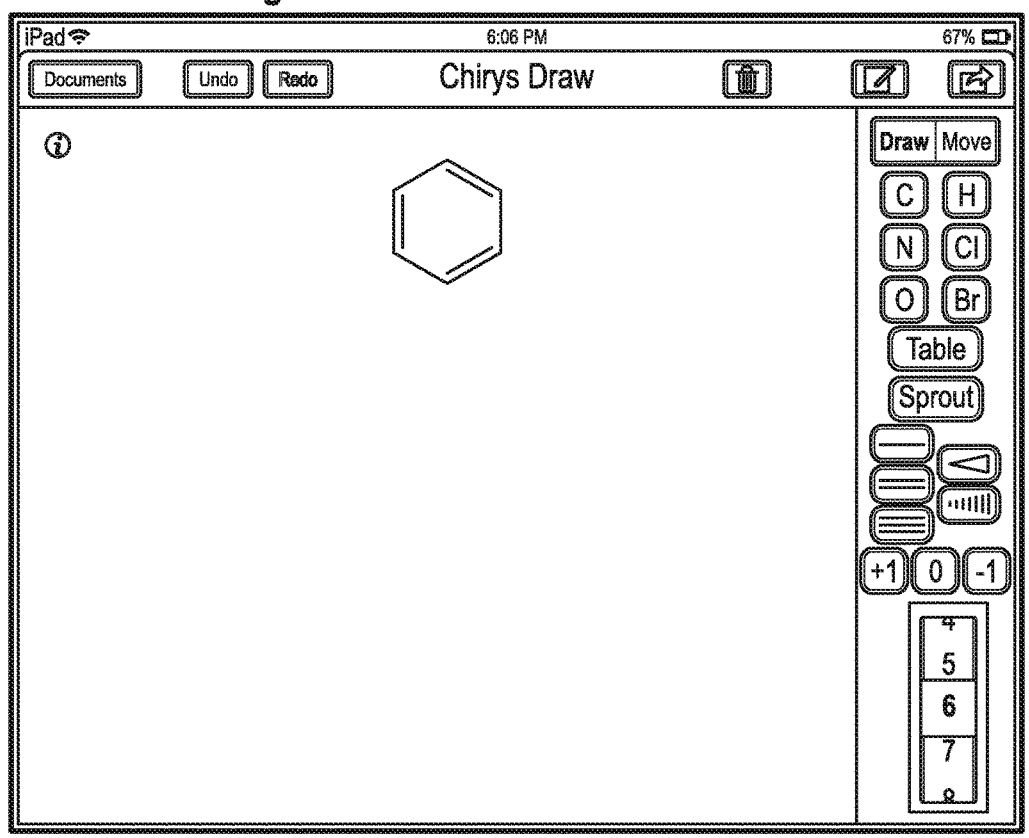
FIG. 13 shows the screen shot of drawing an unsaturated ring.

As shown in FIG. 13, the "Draw Mode" may first be chosen by a user. Choosing a "Draw Mode" may be accomplished by operating the touch-screen with a particular gesture, such as tapping on a particular icon, "Draw", on the display. The number wheel is set to the desired number of carbon atoms to be placed in the ring. Creating an unsaturated ring may be accomplished by operating the touch-screen with a particular gesture, the two fingered circle gesture on the touch screen. The machine then interprets the gesture as a circle, retrieves the commands for the operation from the Gesture Dictionary, and then executes the desired movement, as visualized on the display screen.

It is especially advantageous to combine the unsaturated ring formation gesture and response as follows. The typical gesture used for creating or adding an unsaturated ring is tracing a circle with a two fingers in either a clockwise or counterclockwise direction. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms to be placed in the ring. Creating an unsaturated ring may be accomplished by operating the touch-screen with a particular gesture, the two fingered circle gesture on the touch screen. The machine then interprets the gesture as a circle, retrieves the commands for the operation from the Gesture Dictionary, and then executes the desired movement, as visualized on the display screen. An unsaturated ring is observed to have been drawn in relation to any part of the overall system.

Appending an unsaturated ring may be accomplished by operating the touch-screen with a particular gesture. As described in Table 2, the typical gesture used for appending an unsaturated ring is tracing a circle with a two fingers in either a clockwise or counterclockwise direction.

Figure 14:
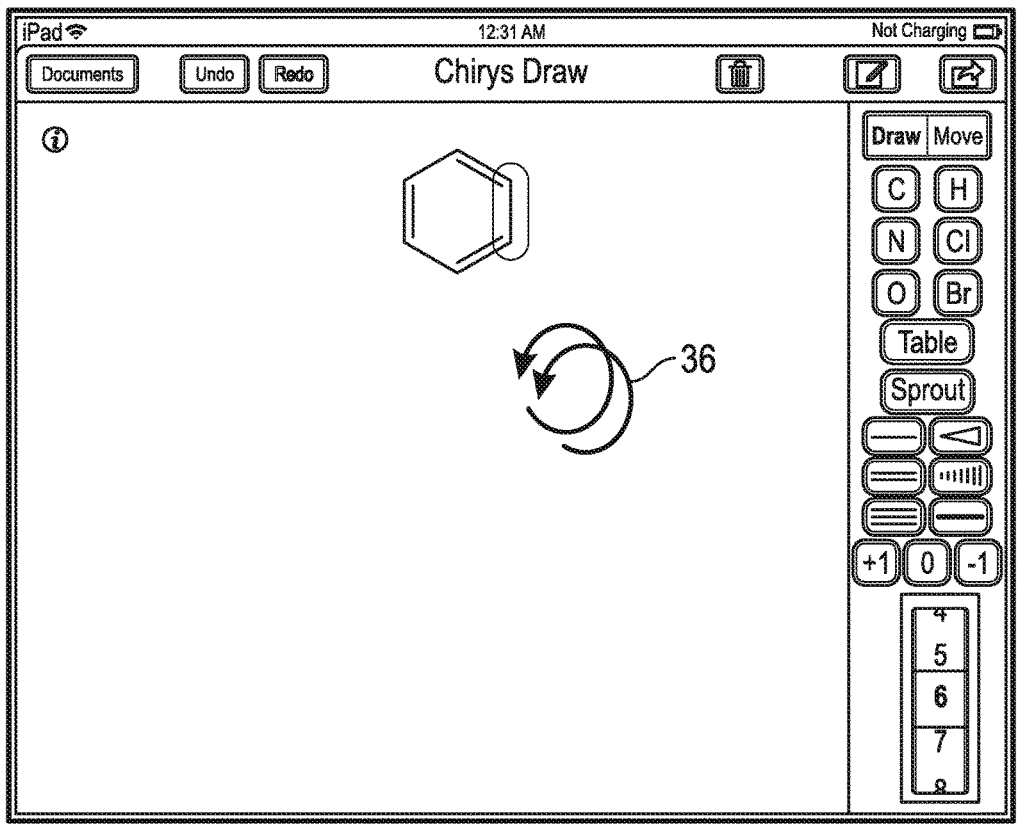
FIG. 14 shows the screen shot of appending an unsaturated ring.
Figure 14:
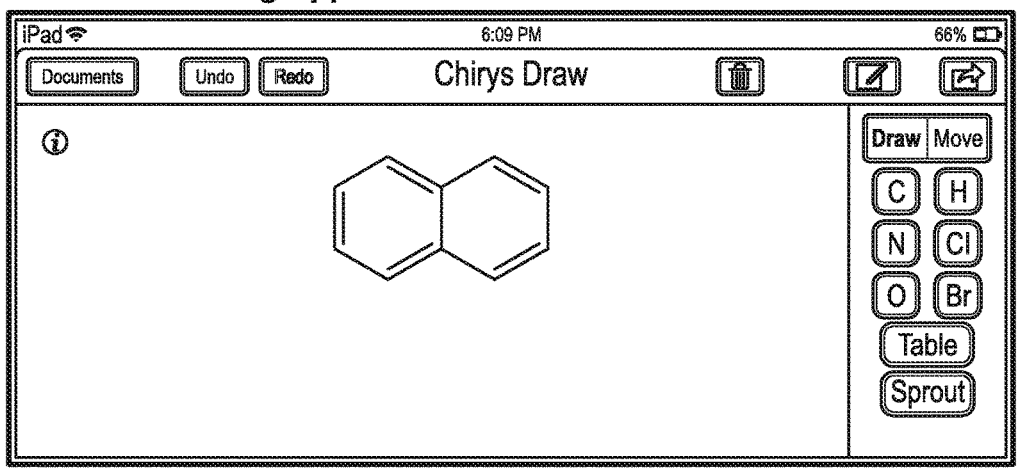

As seen in FIG. 14, the "Draw Mode" may first be chosen by a user. Choosing a "Draw Mode" may be accomplished by operating the touch-screen with a particular gesture, such as tapping on a particular icon, "Draw", on the display. The number wheel is set to the desired number of carbon atoms to be in the ring. Second, the bond to which the unsaturated ring is to be appended is selected by a single tap. Appending an unsaturated ring may be accomplished by operating the touch-screen with a particular gesture, drawing a two fingered circle on the touch screen as shown by arrows 36 (the same gesture as described with respect to FIG. 13, but not shown in FIG. 13). The machine then interprets the gesture as a two fingered circle, retrieves the commands for the operation from the Gesture Dictionary, and then executes the desired movement, as visualized on the display screen.

It is especially advantageous to combine the "append unsaturated ring gesture" and response as follows. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms to be placed in the ring. Second, the bond to which the unsaturated ring is to be appended is selected by a single tap. Appending an unsaturated ring may be accomplished by operating the touch-screen with a particular gesture, drawing a two fingered circle on the touch screen. The machine then interprets the gesture as a two fingered circle, retrieves the commands for the operation from the Gesture Dictionary, and then executes the desired movement, as visualized on the display screen. An unsaturated ring is observed to have been appended in relation to the previously drawn ring and to any other parts of the overall system.

Creating ring closure from two selected atoms contained in a longer chain may be accomplished by operating the touch-screen with a particular gesture. As described in Table 2, a suitable gesture used to close the ring is a single tap on the desired bond modifier button such as a button having a single bond symbol.

Figure 15:
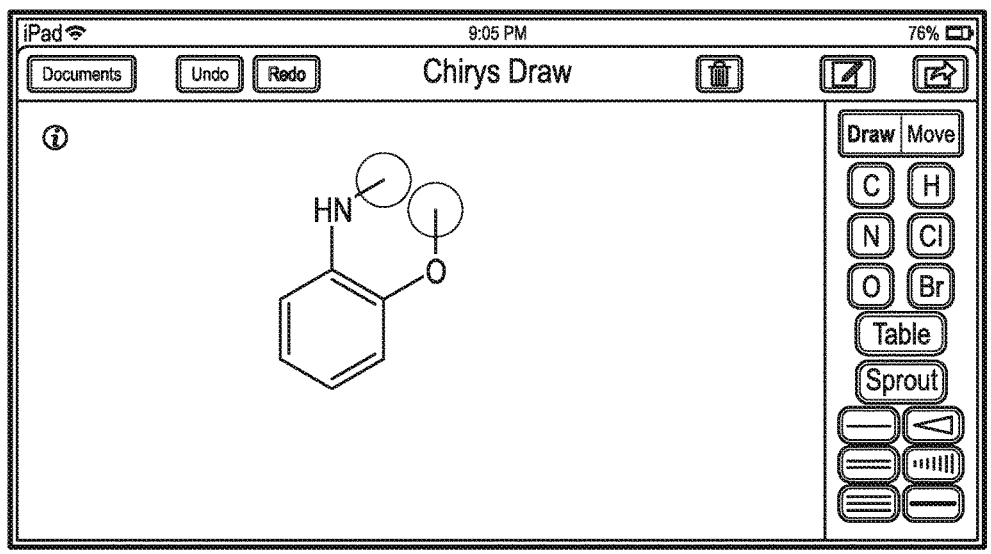
FIG. 15 shows the screen shot of creating a ring closure from two selected atoms contained in a longer chain.
Figure 15:
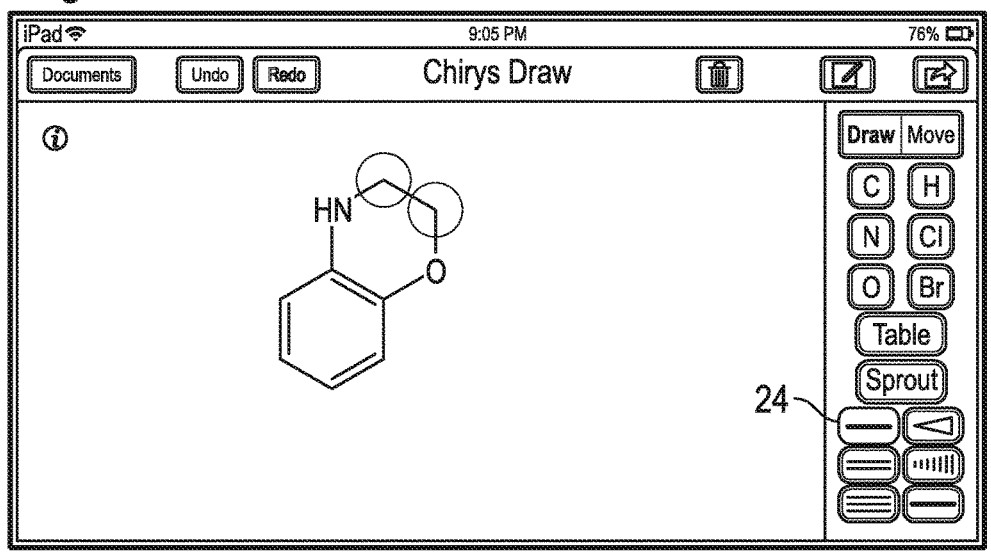

As shown in FIG. 15, the "Draw Mode" may first be chosen by a user. Choosing a "Draw Mode" may be accomplished by operating the touch-screen with a particular gesture, such as tapping on a particular icon, "Draw", on the display. Second, the two atoms to be connected through the bond are selected by a single tap to each atom. Closing the ring through bond addition may be accomplished by operating the touch-screen with a particular gesture, a single tap on the screen of the desired bond modifier button (such as single bond button 24). The machine then interprets the gesture as a single tap, retrieves the commands for the operation from the Gesture Dictionary, and then executes the desired ring closure, as visualized on the display screen.

It is especially advantageous to combine the creating ring closure from two selected atoms gesture and response as follows. First, the "Draw Mode" may be chosen by a user. Choosing a "Draw Mode" may be accomplished by operating the touch-screen with a particular gesture, such as tapping on a particular icon, "Draw", on the display. Second, the two atoms to be connected through the bond are selected by a single tap to each atom. Closing the ring through bond addition may be accomplished by operating the touch-screen with a particular gesture, a single tap on the screen of the desired bond modifier button. The machine then interprets the gesture as a single tap, retrieves the commands for the operation from the Gesture Dictionary, and then executes the desired ring closure, as visualized on the display screen. A new ring is observed to have been created by the ring closure of the selected two atoms in relation to the previously drawn bond and to any other parts of the overall system.

Creating an intermolecular bond from two selected atoms from two distinct molecules may be accomplished by operating the touch-screen with a particular gesture. As described in Table 2, the typical gesture used to close the ring is a single tap on the desired bond modifier button.

Figure 16:
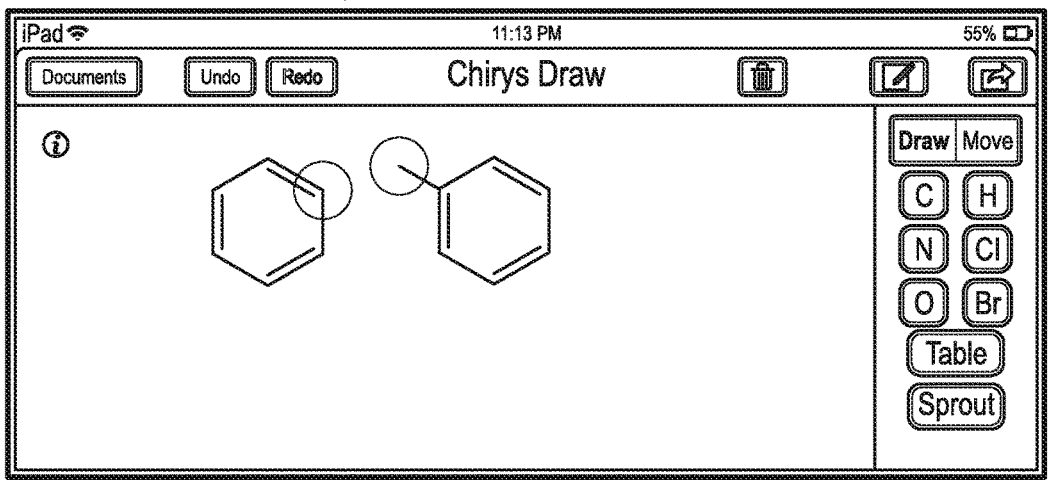
FIG. 16 shows the screen shot of creating an intermolecular bond from two selected atoms from two distinct molecules.
Figure 16:
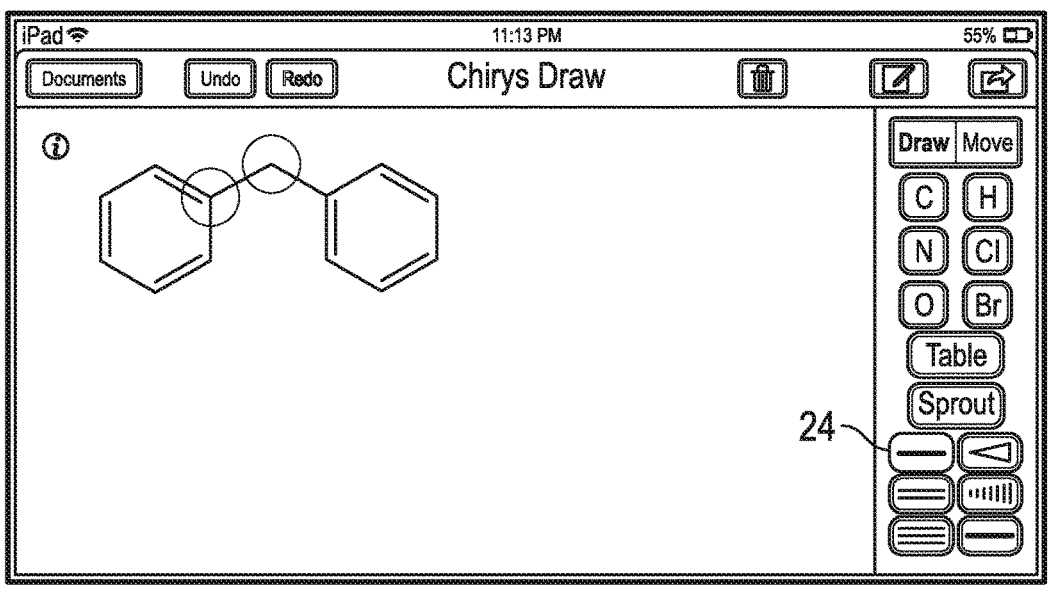

As seen in FIG. 16, the "Draw Mode" may first be chosen by a user. Choosing a "Draw Mode" may be accomplished by operating the touch-screen with a particular gesture, such as tapping on a particular icon, "Draw", on the display. Second, the two atoms to be connected through the bond are selected by a single tap to each atom. Creating the intermolecular bond from two selected atoms from two distinct molecules may be accomplished by operating the touch-screen with a particular gesture, a single tap on the screen of the desired bond modifier button (such as single bond button 24). The machine then interprets the gesture as a single tap, retrieves the commands for the operation from the Gesture Dictionary, and then executes the desired intermolecular bond formation, as visualized on the display screen.

It is especially advantageous to combine the gesture to create an intermolecular bond from two selected atoms from two distinct molecules and the response as follows. First, the "Draw Mode" may be chosen by a user. Choosing a "Draw Mode" may be accomplished by operating the touch-screen with a particular gesture, such as tapping on a particular icon, "Draw", on the display. Second, the two atoms to be connected through the bond are selected by a single tap to each atom. Creating the intermolecular bond from two selected atoms from two distinct molecules may be accomplished by operating the touch-screen with a particular gesture, a single tap on the screen of the desired bond modifier button. The machine then interprets the gesture as a single tap, retrieves the commands for the operation from the Gesture Dictionary, and then executes the desired intermolecular bond formation, as visualized on the display screen. A new bond is observed to have been created between the two selected atoms, thereby creating one molecule from the two molecules in relation to the previously drawn bond and to any other parts of the overall system.

Creating a saturated chain may be accomplished by operating the touch-screen with a particular gesture. As described in Table 2, a suitable gesture used for creating a saturated chain is by a one fingered swipe to either the right or left.

Figure 17:
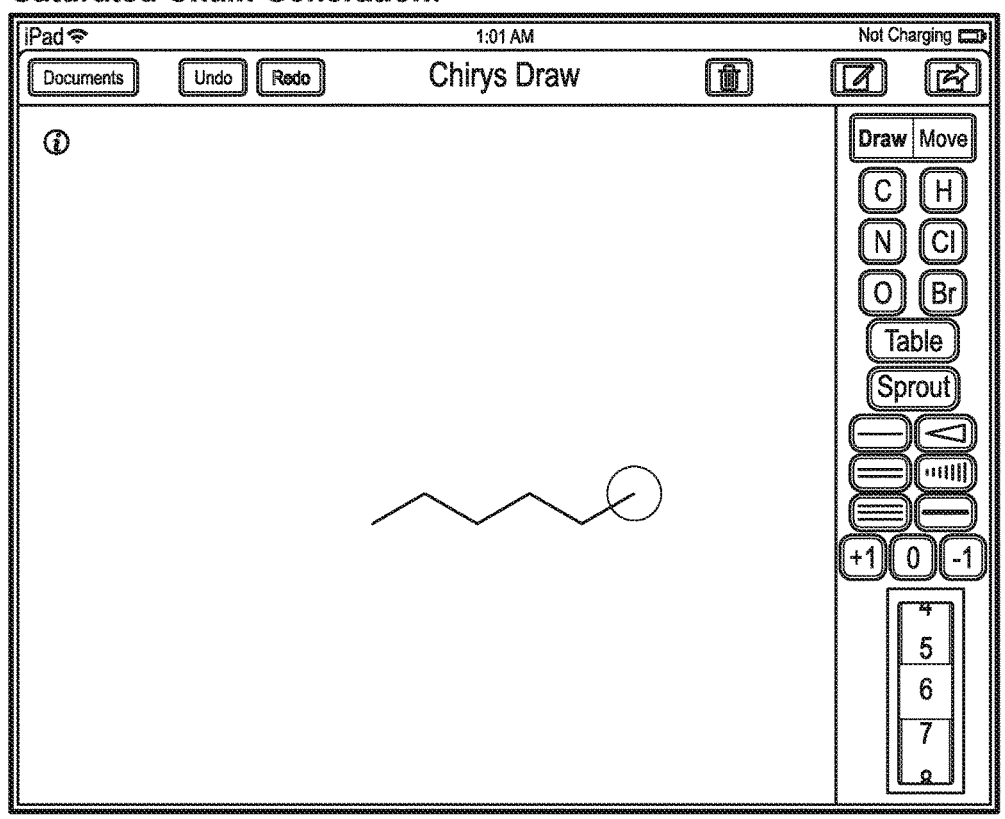
FIG. 17 shows the screen shots of creating a saturated chain.

As seen in FIG. 17, the "Draw Mode" may first be chosen by a user. Choosing a "Draw Mode" may be accomplished by operating the touch-screen with a particular gesture, such as tapping on a particular icon, "Draw", on the display. A number wheel may be set to the desired number of carbon atoms to be added. Creating a saturated chain may be accomplished by operating the touch-screen with a particular gesture, a one fingered swipe to either the right or the left. The machine then interprets the gesture as a one fingered swipe, retrieves the commands for the operation from the Gesture Dictionary, and then executes the desired movement, as visualized on the display screen.

It is especially advantageous to combine the saturated chain formation gesture and response as follows. Creating a saturated chain may be accomplished by operating the touch-screen with a particular gesture. The typical gesture used for creating or adding a saturated chain is by a one fingered swipe to either the right or left. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms to be added. Creating a saturated chain may be accomplished by operating the touch-screen with a particular gesture, a one fingered swipe to either the right or the left. The machine then interprets the gesture as a one fingered swipe, retrieves the commands for the operation from the Gesture Dictionary, and then executes the desired chain generation, as visualized on the display screen. A saturated chain is observed to have been drawn in relation to other parts of the overall system.

Appending a saturated chain may be accomplished by operating the touch-screen with a particular gesture. As described in Table 2, the typical gesture used for appending a saturated chain is a one fingered swipe to either the right or left.

Figure 18:
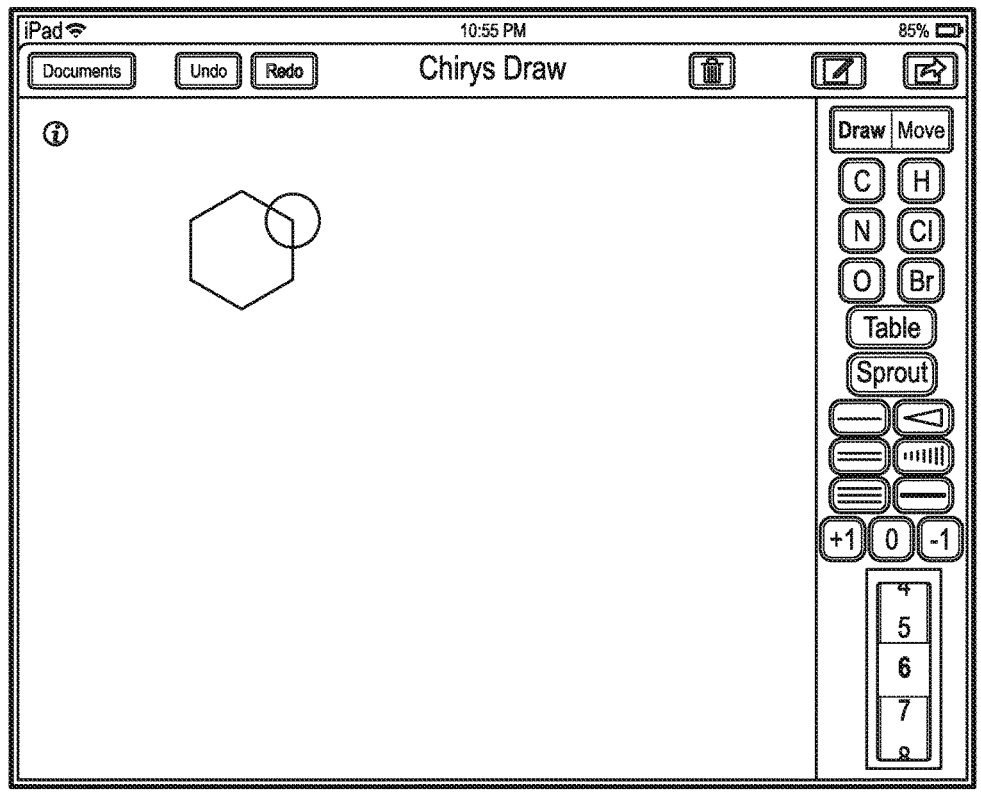
FIG. 18 shows the screen shot of appending a saturated chain.
Figure 18:
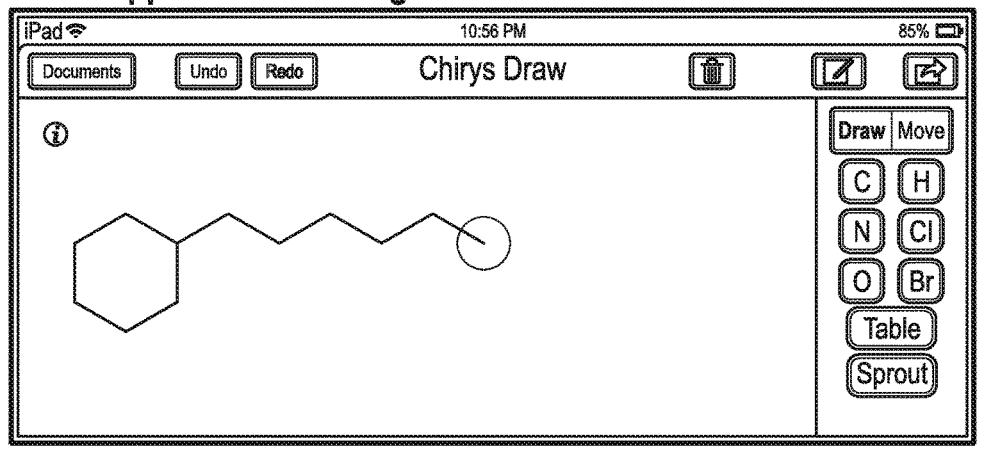

As seen in FIG. 18, the "Draw Mode" may first be chosen by a user. Choosing a "Draw Mode" may be accomplished by operating the touch-screen with a particular gesture, such as tapping on a particular icon, "Draw", on the display. The number wheel is set to the desired number of carbon atoms to be added. Second, the atom to which the saturated chain is to be appended is selected by a single tap. Appending a saturated chain may be accomplished by operating the touch-screen with a particular gesture, single fingered swipe to the left or right. The machine then interprets the gesture as a single fingered swipe, retrieves the commands for the operation from the Gesture Dictionary, and then executes the desired chain generation, as visualized on the display screen.

It is especially advantageous to combine the append chain gesture and response as follows. Appending a saturated chain may be accomplished by operating the touch-screen with a particular gesture. The typical gesture used for appending a saturated chain is a single fingered swipe to either the right or left. First, the "Draw Mode" may be chosen by a user. Choosing a "Draw Mode" may be accomplished by operating the touch-screen with a particular gesture, such as tapping on a particular icon, "Draw", on the display. The number wheel is set to the desired number of carbon atoms to be added. Second, the atom to which the saturated chain is to be appended is selected by a single tap. Appending a saturated chain may be accomplished by operating the touch-screen with a particular gesture, single fingered swipe to the left or right. The machine then interprets the gesture as a single fingered swipe, retrieves the commands for the operation from the Gesture Dictionary, and then executes the desired chain generation, as visualized on the display screen. A saturated chain is observed to have been appended to the selected atom in relation to the previously drawn molecule and to any other parts of the overall system.

Figure 19:
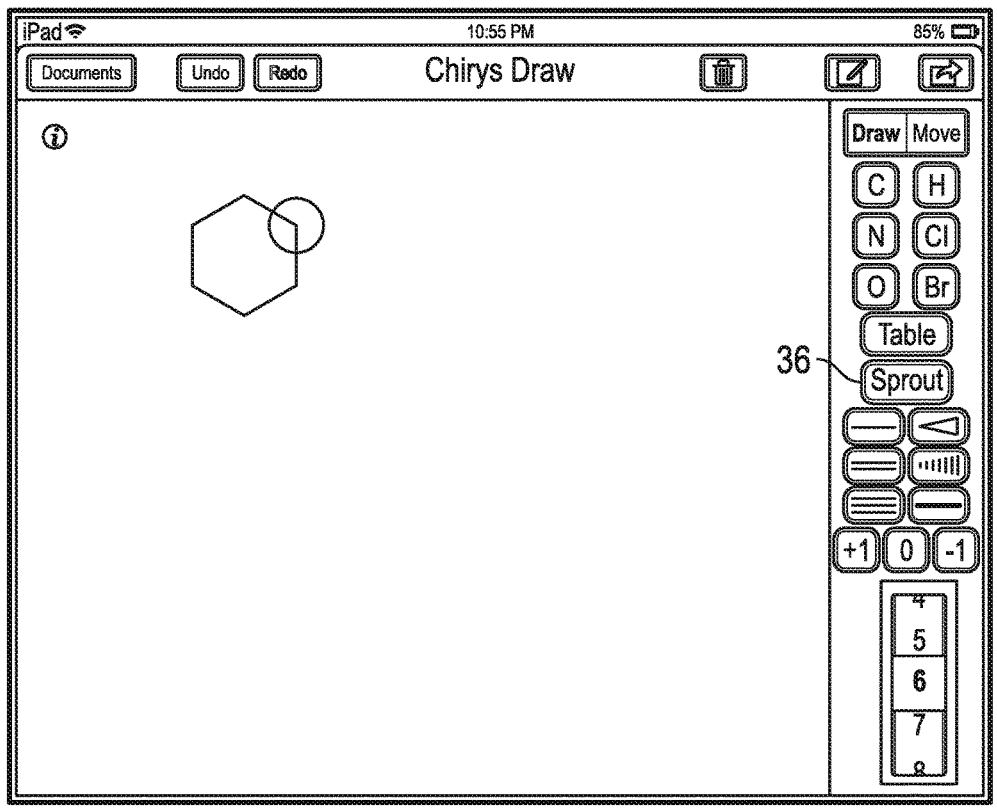
FIG. 19 shows the sprouting a methyl group.
Figure 19:
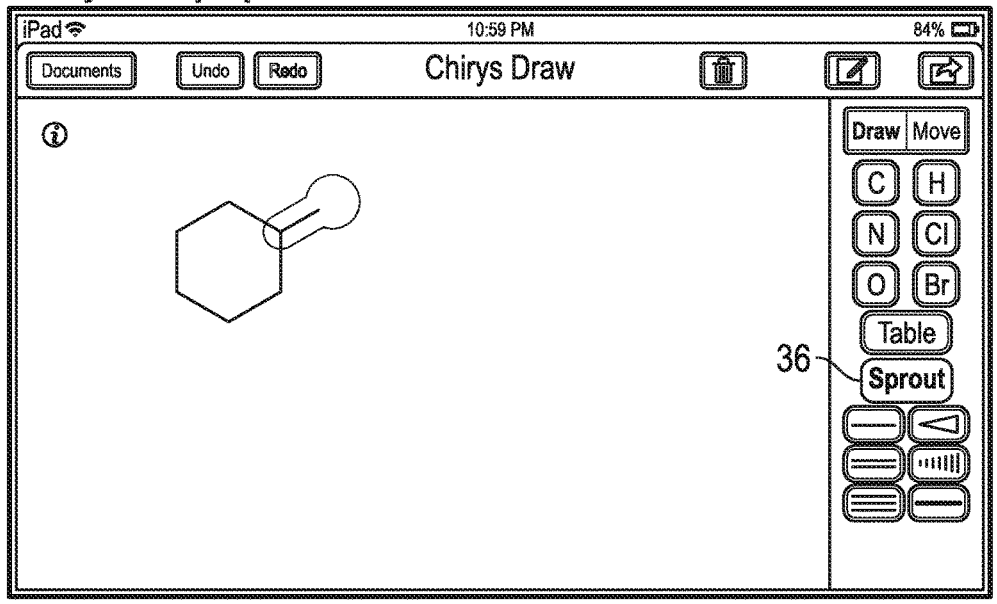

Sprouting a methyl group may be accomplished by operating the touch-screen with a particular gesture. As described in Table 2, a suitable gesture used for adding a methyl group is a single fingered tap on the "Sprout" button 36. The "Sprout" button provides an extremely facile manner in which to add one carbon atom to a molecular structure. For example, the "Sprout" button can be quickly used to add a carbon atom that can be changed to another atom, e.g. oxygen atom, or further extended as a pendant side chain. As shown in FIG. 19, the "Draw Mode" may first be chosen by a user. Choosing a "Draw Mode" may be accomplished by operating the touch-screen with a particular gesture, such as tapping on a particular icon, "Draw", on the display. The atom to which the methyl is to be appended is selected by a single tap. Adding a methyl group may be accomplished by operating the touch-screen with a particular gesture, a single fingered tap on the "Sprout" button. The machine then interprets the gesture as a single fingered tap, retrieves the commands for the operation from the Gesture Dictionary, and then executes the desired methyl group formation, as visualized on the display screen.

It is especially advantageous to combine the sprout methyl gesture and response as follows. Sprouting a methyl group may be accomplished by operating the touch-screen with a particular gesture. The suitable gesture used for adding a methyl group is by a single fingered tap on the "Sprout" button. First, the "Draw Mode" may be chosen by a user. Choosing a "Draw Mode" may be accomplished by operating the touch-screen with a particular gesture, such as tapping on a particular icon, "Draw", on the display. The atom to which the methyl is to be appended is selected by a single tap. Adding a methyl group may be accomplished by operating the touch-screen with a particular gesture, a single fingered tap on the "Sprout" button. The machine then interprets the gesture as a single fingered tap, retrieves the commands for the operation from the Gesture Dictionary, and then executes the desired methyl group formation, as visualized on the display screen. A methyl group is observed to have been drawn on the selected atom in relation to any other parts of the overall system.

Appending a gem-dimethyl group may be accomplished by operating the touch-screen with a particular gesture. As described in Table 2, a suitable gesture used for appending gem-dimethyl group is a single fingered checkmark.

Figure 20:
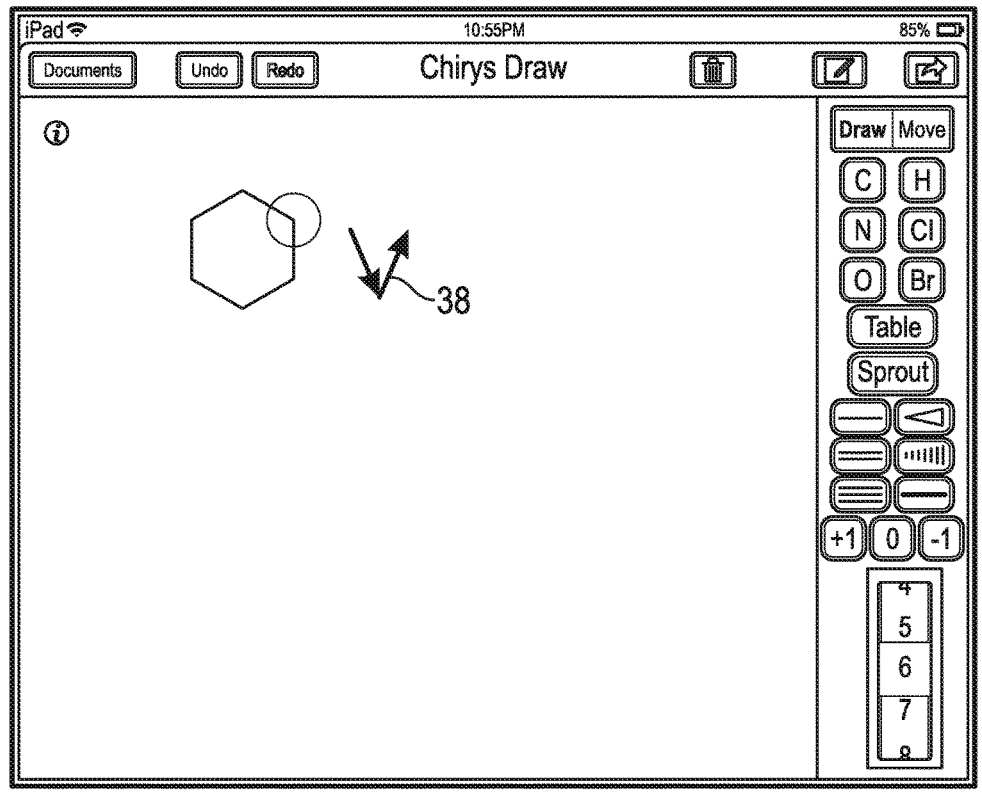
FIG. 20 shows the appending a gem-dimethyl group.
Figure 20:
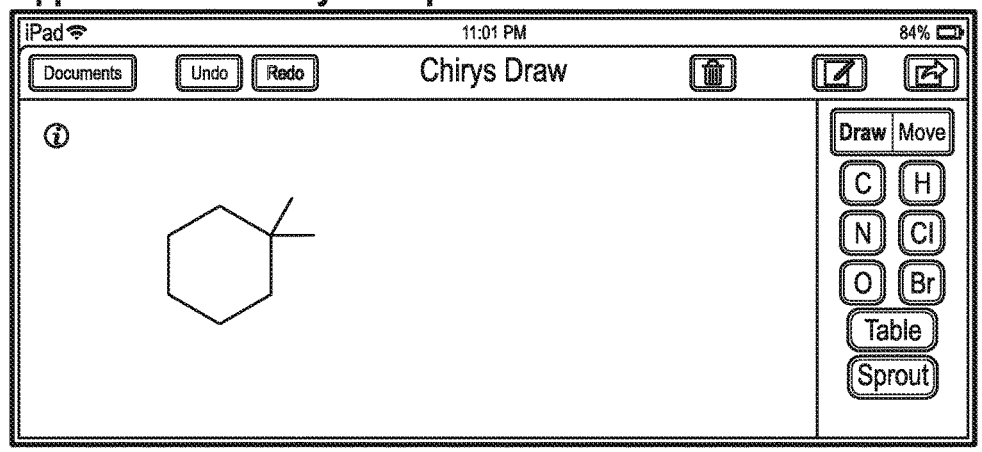

As shown in FIG. 20, the "Draw Mode" may first be chosen by a user. Choosing a "Draw Mode" may be accomplished by operating the touch-screen with a particular gesture, such as tapping on a particular icon, "Draw", on the display. Second, the atom to which the gem-dimethyl is to be appended is selected by a single tap. Appending a gem-dimethyl group may be accomplished by operating the touch-screen with a particular gesture, tracing a "checkmark" on the screen with a single finger as denoted by the arrows 38. The checkmark includes two approximately linear non-parallel line segments connected at a vertex. The endpoint of the first line forms the start of the second. The open side of the checkmark may be in any orientation, and the lengths of the sides may be any relative length, possibly forming, for example, a V shape. The machine then interprets the gesture as a checkmark, retrieves the commands for the operation from the Gesture Dictionary, and then executes the desired movement, as visualized on the display screen.

It is especially advantageous to combine the "checkmark gesture" and response as follows. Appending a gem-dimethyl group may be accomplished by operating the touch-screen with a particular gesture. The suitable gesture used for appending gem-dimethyl group is a single fingered checkmark. First, the "Draw Mode" may be chosen by a user. Choosing a "Draw Mode" may be accomplished by operating the touch-screen with a particular gesture, such as tapping on a particular icon, "Draw", on the display. Second, the atom to which the gem-dimethyl is to be appended is selected by a single tap. Appending a gem-dimethyl group may be accomplished by operating the touch-screen with a particular gesture, tracing a "checkmark" on the screen with a single finger. The machine then interprets the gesture as a checkmark, retrieves the commands for the operation from the Gesture Dictionary, and then executes the desired movement, as visualized on the display screen. A gem-dimethyl group is observed to have been appended in relation to the previously drawn atom and to any other parts of the overall system. The V or checkmark gesture is convenient for the user as it simulates the shape of the added two methyl groups on the chemical structure symbol.

Moving an attached group may be accomplished by operating the touch-screen with a particular gesture. As described in Table 2, a suitable gesture used for switching the group alignment is a two fingered swipe to the right or left.

Figure 21:
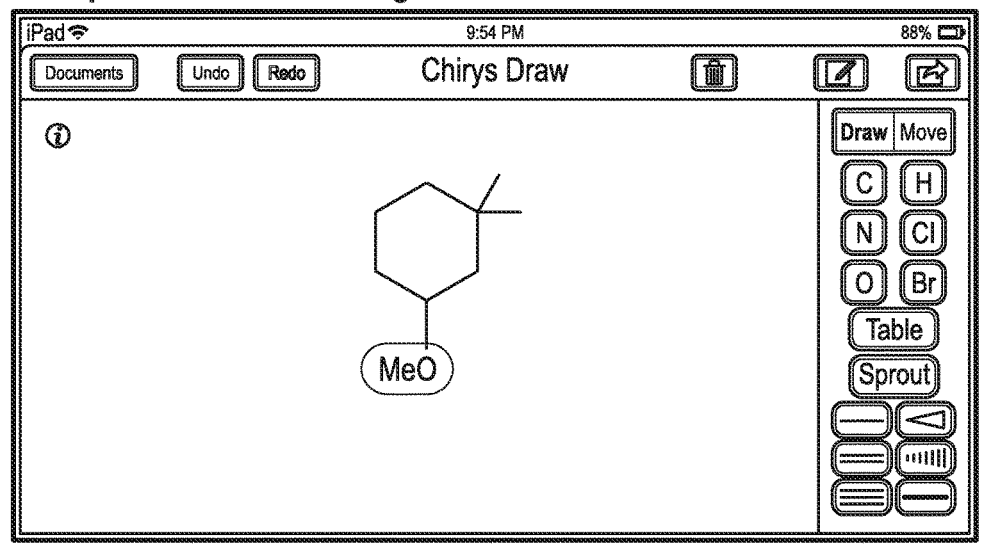
FIG. 21 shows the attached group alignment.
Figure 21:
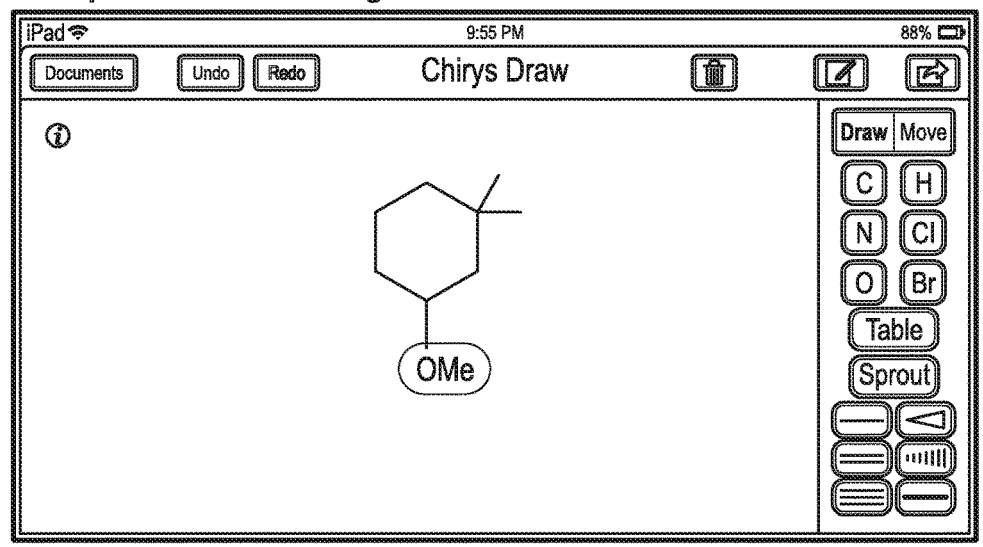

As shown in FIG. 21, the "Draw Mode" may first be chosen by a user. Choosing a "Draw Mode" may be accomplished by operating the touch-screen with a particular gesture, such as tapping on a particular icon, "Draw", on the display. Second, the group that will be realigned is selected by a single tap. Group alignment may be accomplished by operating the touch-screen with a particular gesture, a two fingered swipe to the right or left on the screen. The machine then interprets the gesture as a two fingered swipe, retrieves the commands for the operation from the Gesture Dictionary, and then executes the desired movement, as visualized on the display screen.

It is especially advantageous to combine the group alignment two fingered swipe and response as follows. Interprets gesture as swipe gesture, retrieves commands for operation and executes the desired group alignment movement, with visualization on display screen. First, the "Draw Mode" may be chosen by a user. Choosing a "Draw Mode" may be accomplished by operating the touch-screen with a particular gesture, such as tapping on a particular icon, "Draw", on the display. Second, the group that will be realigned is selected by a single tap. Group alignment may be accomplished by operating the touch-screen with a particular gesture, two fingered swipe to the right or left on the screen. The machine then interprets the gesture as a two fingered swipe, retrieves the commands for the operation from the Gesture Dictionary, and then executes the desired movement, as visualized on the display screen. The group is observed to have been realigned in relation to the previously drawn atom and to any other parts of the overall system.

Cis-trans isomerization of an alkene not contained in a ring may be accomplished by operating the touch-screen with a particular gesture. As described in Table 2, a suitable gesture used for switching the group alignment is a two fingered swipe to the right or left.

Figure 22:
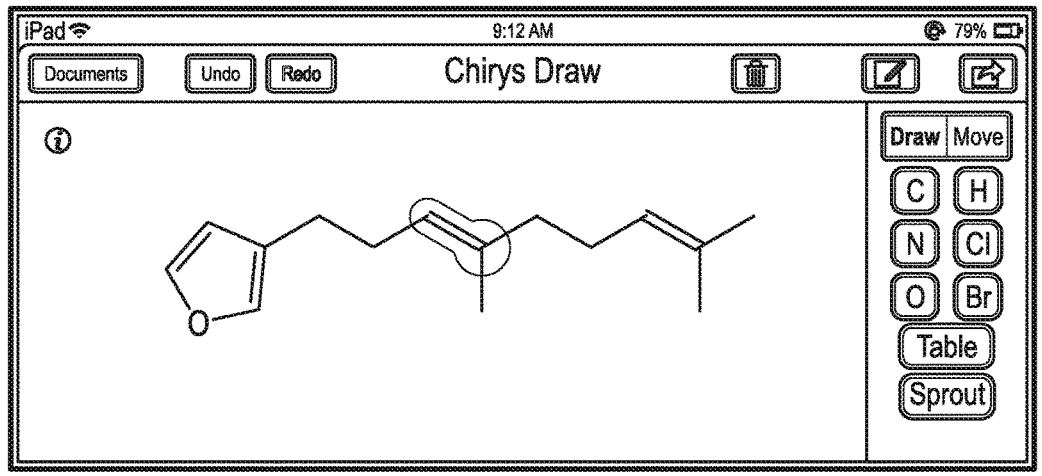
FIG. 22 shows the cis-trans isomerization of an alkene not contained in a ring.
Figure 22:
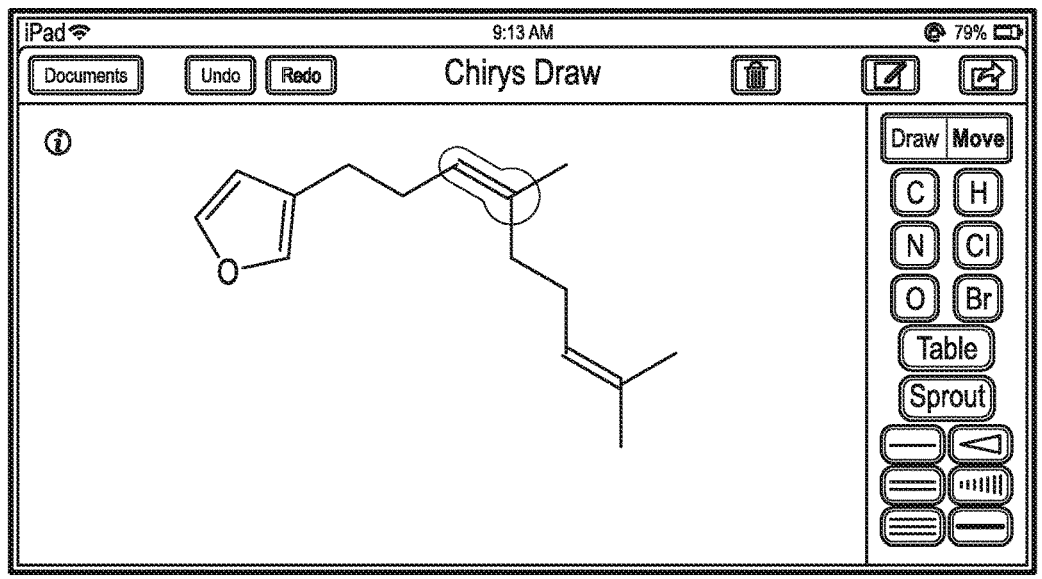

As shown in FIG. 22, the "Move Mode" may first be chosen by a user. Choosing a "Move Mode" may be accomplished by operating the touch-screen with a particular gesture, such as tapping on a particular icon, "Move", on the display. Second, the double bond to be isomerized and the atom where the two "R Groups" will be exchanged are selected by a single tap on each. Cis-trans isomerization may be accomplished by operating the touch-screen with a particular gesture, two fingered swipe to the right or left on the screen. The machine then interprets the gesture as a two fingered swipe, retrieves the commands for the operation from the Gesture Dictionary, and then executes the desired cis-trans isomerization movement, as visualized on the display screen.

It is especially advantageous to combine the cis-trans isomerization two fingered swipe and response as follows. Switching a double bond between cis and trans orientation of an alkene not contained in a ring may be accomplished by operating the touch-screen with a particular gesture. The typical gesture used for switching the group alignment is a two fingered swipe to the right or left. First, the "Move Mode" may be chosen by a user. Choosing a "Move Mode" may be accomplished by operating the touch-screen with a particular gesture, such as tapping on a particular icon, "Move", on the display. Second, the double bond to be isomerized and the atom where the two "R Groups" will be exchanged are selected by a single tap on each. Cis-trans isomerization may be accomplished by operating the touch-screen with a particular gesture, two fingered swipe to the right or left on the screen. The machine then interprets the gesture as a two fingered swipe, retrieves the commands for the operation from the Gesture Dictionary, and then executes the desired cis-trans isomerization movement, as visualized on the display screen. The two attached R groups are observed to have been switched in orientation to the previously drawn unsaturated bond and to any other parts of the overall system.

Editing a formal charge can be accomplished by operating the touch-screen with a particular gesture. As described in Table 2, a suitable gesture used for editing a formal charge is a one fingered tap on one of one or more formal charge modifier buttons 42, 44, and 46. With these three buttons +1, 0, and −1, a tap on one of the buttons can add one electronic charge to whatever the current charge state of the selected atom is using the +1 button 42, subtract one electronic charge from whatever the current charge state of the selected atom is using the −1 button 46, or clear the charge on the atom to neutral with the 0 button 44.

Figure 23:
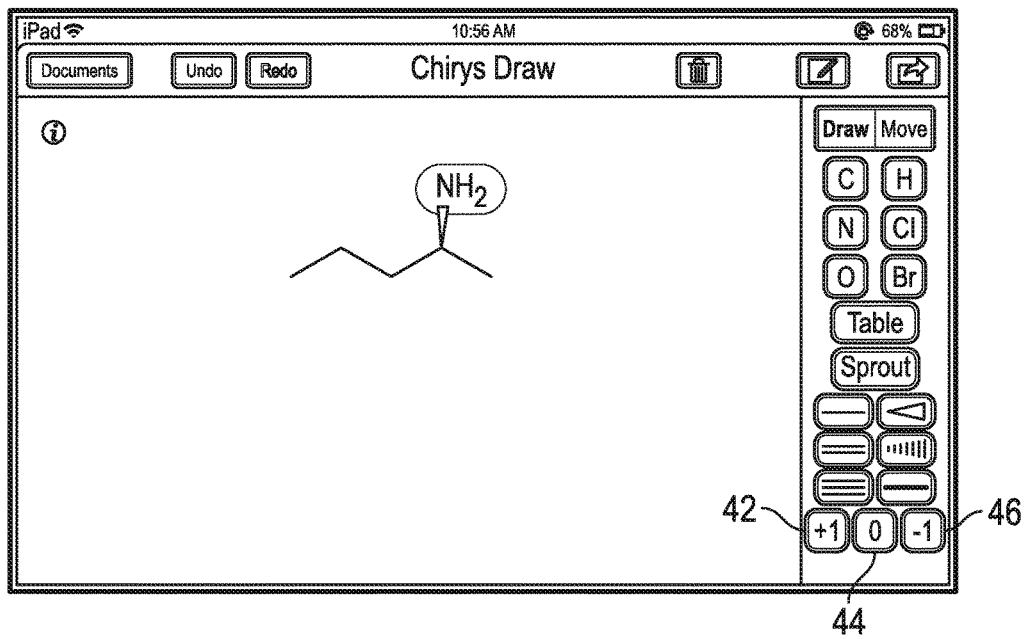
FIG. 23 shows the editing of a formal charge.
Figure 23:
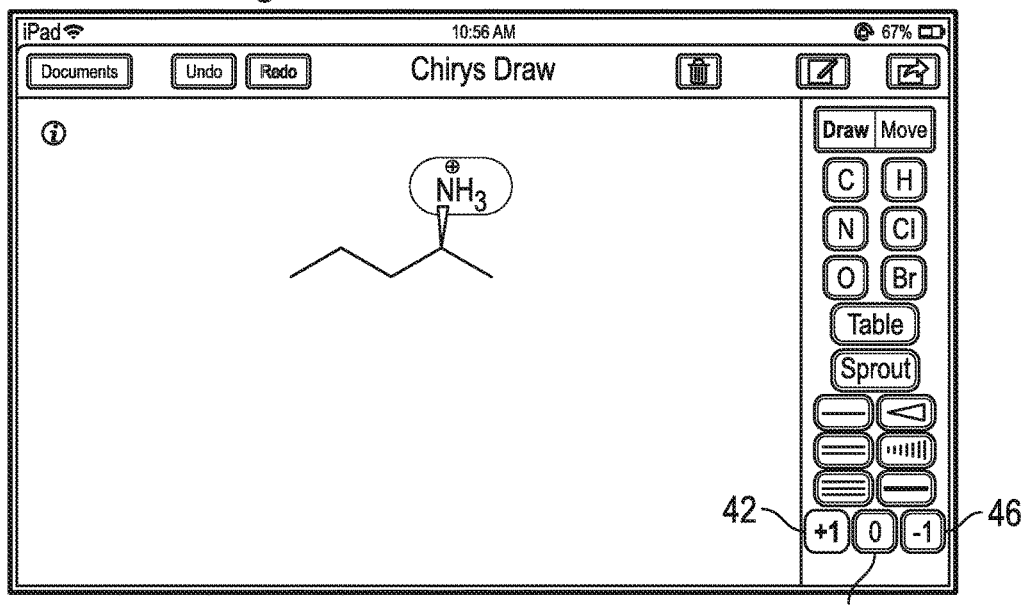

As seen in FIG. 23, the "Draw Mode" may first be chosen by a user. Choosing a "Draw Mode" may be accomplished by operating the touch-screen with a particular gesture, such as tapping on a particular icon, "Draw", on the display. Second, the atom to be edited is selected by a single tap. Editing a formal charge may be accomplished by operating the touch-screen with a particular gesture, a single tap on the screen of the desired formal charge modifier button. The machine then interprets the gesture as a single tap, retrieves the commands for the operation from the Gesture Dictionary, and then executes the desired formal charge edit, as visualized on the display screen.

It is especially advantageous to combine the change formal charge edit gesture and response as follows. Editing formal charge can be accomplished by operating the touch-screen with a particular gesture. The suitable gesture used for editing an atom is a one fingered tap on a formal charge button. First, the "Draw Mode" may be chosen by a user. Choosing a "Draw Mode" may be accomplished by operating the touch-screen with a particular gesture, such as tapping on a particular icon, "Draw", on the display. Second, the atom to be edited is selected by a single tap. Editing a formal charge may be accomplished by operating the touch-screen with a particular gesture, a single tap on the screen of the desired formal charge modifier button. The machine then interprets the gesture as a single tap, retrieves the commands for the operation from the Gesture Dictionary, and then executes the desired formal charge edit, as visualized on the display screen. The selected atom is then observed to have the formal charge edited in relation to the selected atom and any other parts of the overall system.

Adding a group abbreviation can be accomplished by operating the touch-screen with a particular gesture. As described in Table 2, a suitable gesture used for adding an abbreviation is a one fingered tap on a group modifier button.

Figure 24:
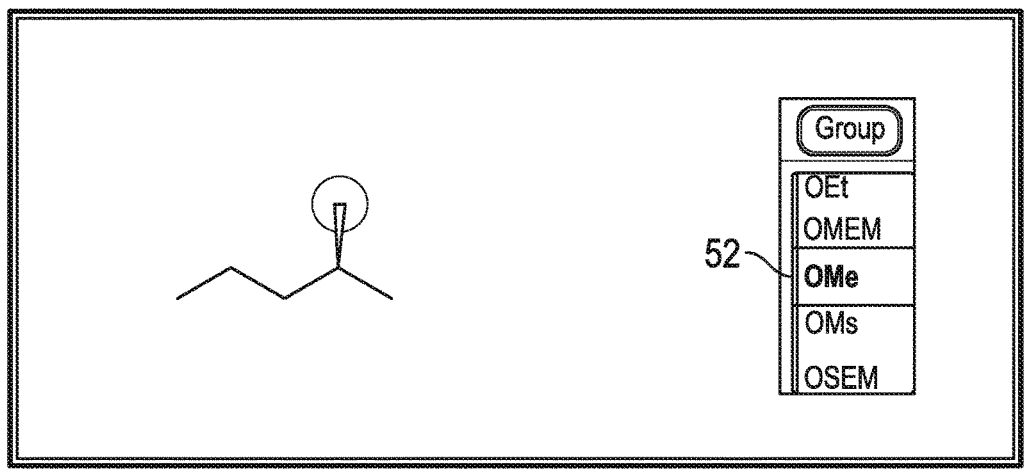
FIG. 24 shows the addition of a group abbreviation.
Figure 24:
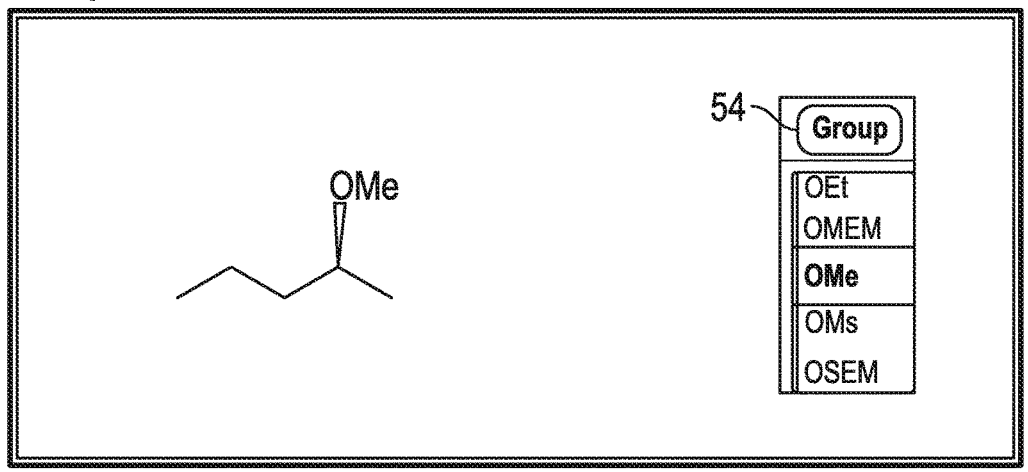

As seen in FIG. 24, the "Draw Mode" may first be chosen by a user. Choosing a "Draw Mode" may be accomplished by operating the touch-screen with a particular gesture, such as tapping on a particular icon, "Draw", on the display. Second, the atom to be edited is selected by a single tap. Adding a group abbreviation may be accomplished by selecting the desired abbreviation on the abbreviation group wheel 52, and then operating the touch-screen with a particular gesture, a single tap on the screen on the group modifier button 54. The machine then interprets the gesture as a single tap, retrieves the commands for the operation from the Gesture Dictionary, and then executes the desired group abbreviation addition, as visualized on the display screen.

It is especially advantageous to combine the group abbreviation gesture and response as follows. Adding a group abbreviation can be accomplished by operating the touch-screen with a particular gesture. The suitable gesture used for adding an abbreviation is a one fingered tap on a group modifier button. First, the "Draw Mode" may be chosen by a user. Choosing a "Draw Mode" may be accomplished by operating the touch-screen with a particular gesture, such as tapping on a particular icon, "Draw", on the display. Second, the atom to be edited is selected by a single tap. Adding a group abbreviation may be accomplished by selecting the desired abbreviation on the abbreviation group wheel, shown below, and then operating the touch-screen with a particular gesture, a single tap on the screen on the group modifier button. The machine then interprets the gesture as a single tap, retrieves the commands for the operation from the Gesture Dictionary, and then executes the desired group abbreviation addition, as visualized on the display screen. The selected atom is then observed to have the group abbreviation added in relation to any other parts of the overall system.

Editing a group abbreviation can be accomplished by operating the touch-screen with a particular gesture. As described in Table 2, a suitable gesture used for adding an abbreviation is a one fingered tap on a group modifier button.

Figure 25:
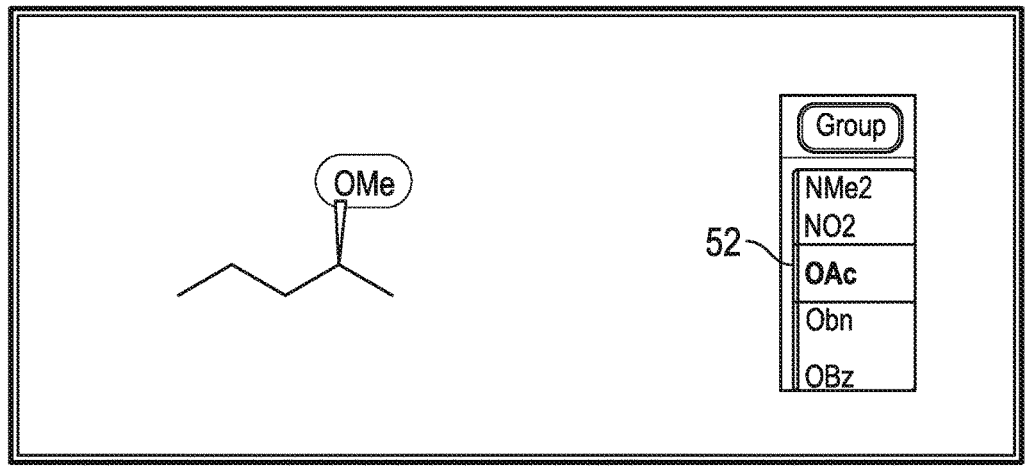
FIG. 25 shows the editing of a group abbreviation.
Figure 25:
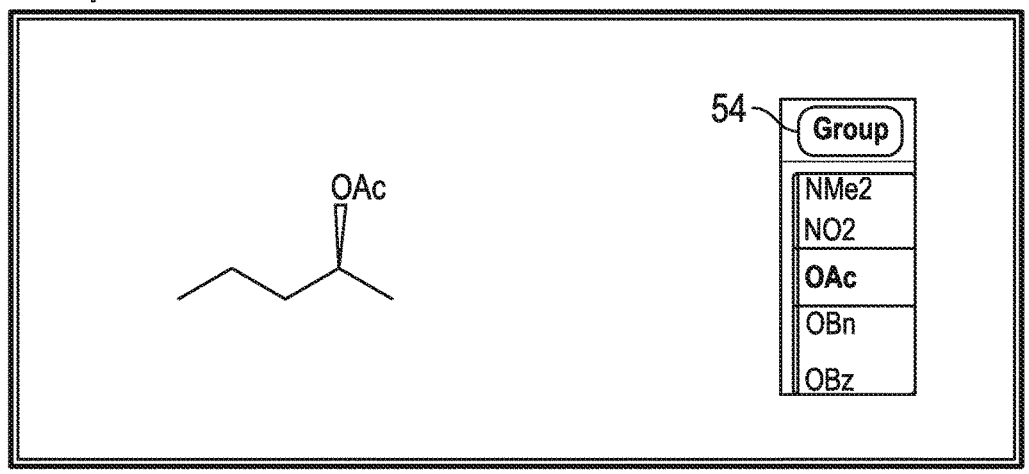

As shown in FIG. 25, the "Draw Mode" may first be chosen by a user. Choosing a "Draw Mode" may be accomplished by operating the touch-screen with a particular gesture, such as tapping on a particular icon, "Draw", on the display. Second, the group to be edited is selected by a single tap. Editing a group abbreviation may be accomplished by selecting the desired abbreviation on the abbreviation group wheel 52, and then operating the touch-screen with a particular gesture, a single tap on the screen on the group modifier button 54. The machine then interprets the gesture as a single tap, retrieves the commands for the operation from the Gesture Dictionary, and then executes the desired group abbreviation edit, as visualized on the display screen.

It is especially advantageous to combine the edit group abbreviation gesture and response as follows. Editing a group abbreviation can be accomplished by operating the touch-screen with a particular gesture. The suitable gesture used for editing an abbreviation is a one fingered tap on a group modifier button. First, the "Draw Mode" may be chosen by a user. Choosing a "Draw Mode" may be accomplished by operating the touch-screen with a particular gesture, such as tapping on a particular icon, "Draw", on the display. Second, the group to be edited is selected by a single tap. Editing a group abbreviation may be accomplished by selecting the desired abbreviation on the abbreviation group wheel, and then operating the touch-screen with a particular gesture, a single tap on the screen on the group modifier button. The machine then interprets the gesture as a single tap, retrieves the commands for the operation from the Gesture Dictionary, and then executes the desired group abbreviation edit, as visualized on the display screen. The selected group is then observed to be updated with the new group abbreviation added in relation to any other parts of the overall system.

Creating a reaction arrow may be accomplished by operating the touch-screen with a particular gesture. As described in Table 2, a suitable gesture used for creating or adding reaction arrow is by a single fingered swipe to either the right or left. The reaction arrow produced with this swipe may be a unidirectional single shafted arrow.

Figure 26:
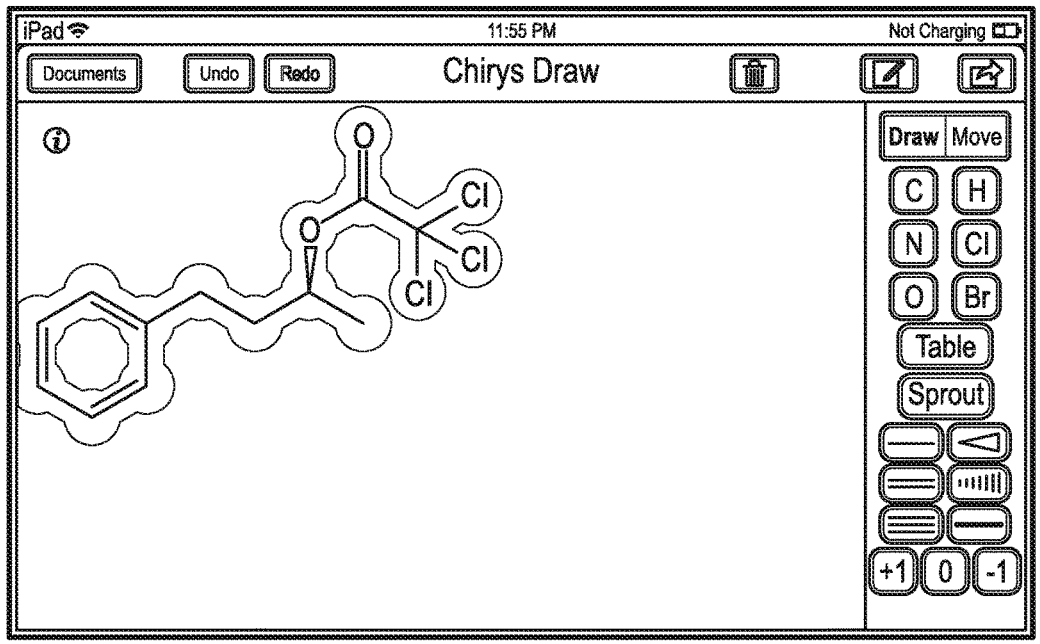
FIG. 26 shows the creation of a reaction arrow.
Figure 26:
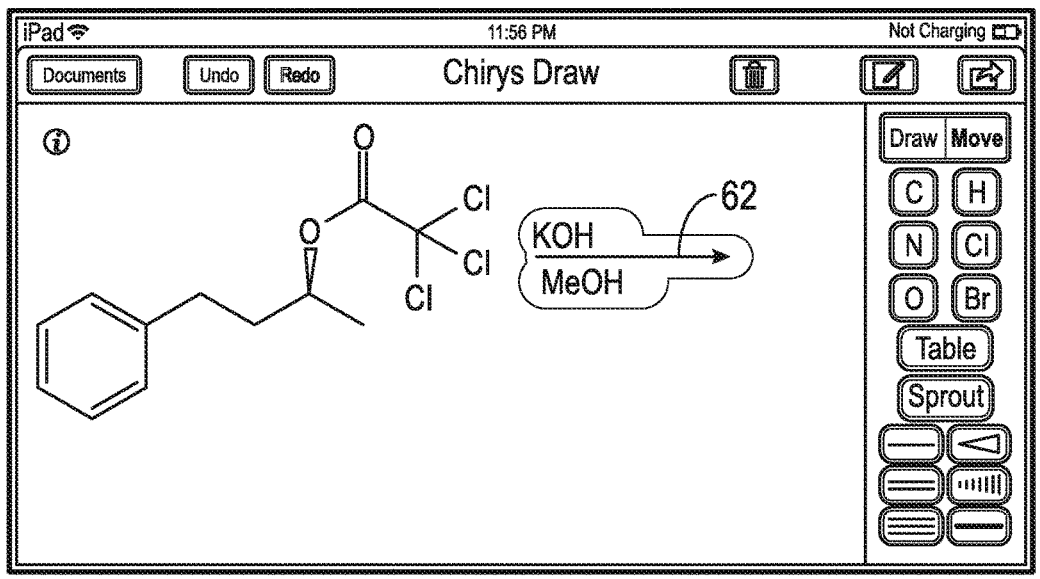

As seen in FIG. 26, the "Draw Mode" may first be chosen by a user. Choosing a "Draw Mode" may be accomplished by operating the touch-screen with a particular gesture, such as tapping on a particular icon, "Draw", on the display. A molecule is selected (e.g. with the double tap as described above), or otherwise denoted, and then operating the touch-screen with a particular gesture, single finger swipe to the left or right. The machine then interprets the gesture as a single fingered swipe, retrieves the commands for the operation from the Gesture Dictionary, and then executes the desired reaction arrow 62 generation, as visualized on the display screen.

It is especially advantageous to combine the create reaction arrow gesture and response as follows. Creating a reaction arrow may be accomplished by operating the touch-screen with a particular gesture. The suitable gesture used for creating or adding reaction arrow is by a swipe to either the right or left. First, the "Draw Mode" may be chosen by a user. Choosing a "Draw Mode" may be accomplished by operating the touch-screen with a particular gesture, such as tapping on a particular icon, "Draw", on the display. A molecule is selected, or otherwise denoted, and then operating the touch-screen with a particular gesture, single finger swipe to the left or right. The machine then interprets the gesture as a swipe, retrieves the commands for the operation from the Gesture Dictionary, and then executes the desired reaction arrow generation, as visualized on the display screen. A reaction arrow is then displayed positioned to the right of the selected molecule and in relation to any non-moving parts of the overall system.

Creating a retrosynthetic reaction arrow, which may be a double shafted arrow, may be accomplished by operating the touch-screen with a particular gesture. As described in Table 2, the typical gesture used for creating or adding this type of reaction arrow is by a double fingered swipe to either the right or left.

Figure 27:
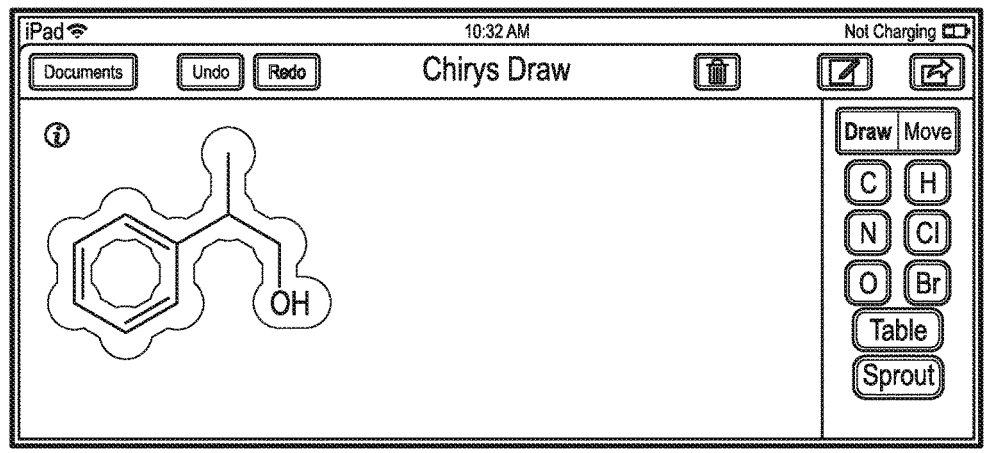
FIG. 27 shows the creation of a retrosynthetic reaction arrow.
Figure 27:
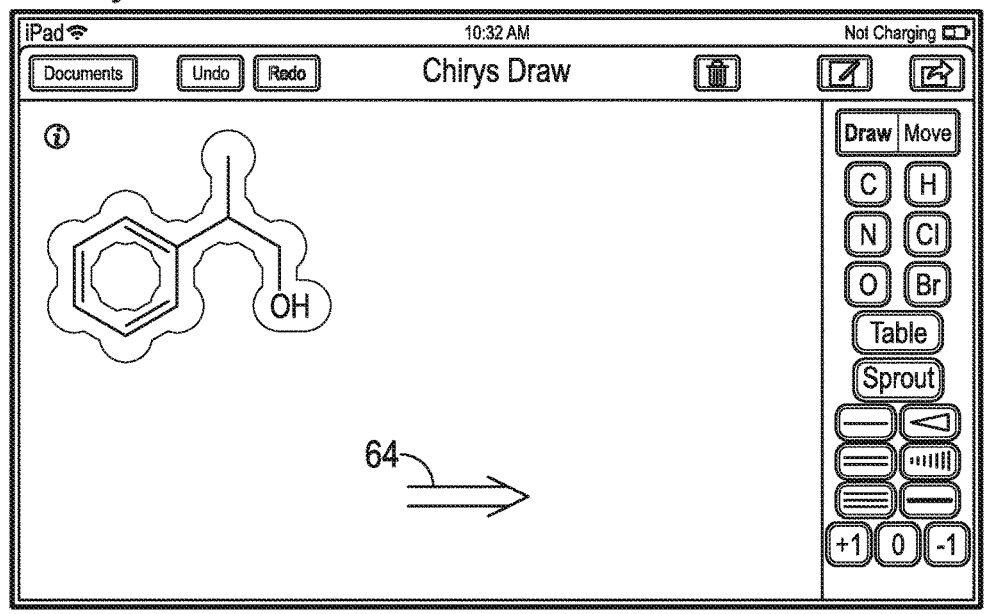

As shown in FIG. 27 the "Draw Mode" may first be chosen by a user. Choosing a "Draw Mode" may be accomplished by operating the touch-screen with a particular gesture, such as tapping on a particular icon, "Draw", on the display. A molecule is selected, or otherwise denoted, and then operating the touch-screen with a particular gesture, double finger swipe to the left or right. The machine then interprets the gesture as a two fingered swipe, retrieves the commands for the operation from the Gesture Dictionary, and then executes the desired retrosynthetic reaction arrow 64 generation, as visualized on the display screen.

It is especially advantageous to combine the create retrosynthetic reaction arrow gesture and response as follows. Creating a retrosynthetic reaction arrow may be accomplished by operating the touch-screen with a particular gesture. The typical gesture used for creating or adding reaction arrow is by a double fingered swipe to either the right or left. First, the "Draw Mode" may be chosen by a user. Choosing a "Draw Mode" may be accomplished by operating the touch-screen with a particular gesture, such as tapping on a particular icon, "Draw", on the display. A molecule is selected, or otherwise denoted, and then operating the touch-screen with a particular gesture, double finger swipe to the left or right. The machine then interprets the gesture as a two fingered swipe, retrieves the commands for the operation from the Gesture Dictionary from the Gesture Dictionary, and then executes the desired movement, as visualized on the display screen. A retrosynthetic reaction arrow is then displayed positioned to the right of the selected molecule and in relation to any non-moving parts of the overall system.

Figure 28A:
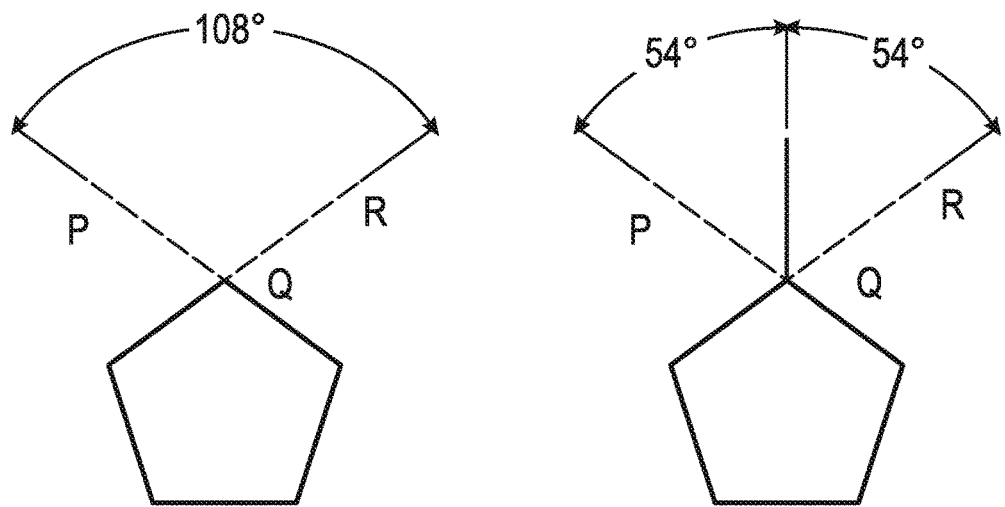
FIG. 28A shows the extension of a bond from an atom having two connections in a ring.

As shown in FIG. 28A, for the addition of an atom to a ring or chain, the first atom added to the ring or chain will be located by the bisected angle between the coordinates shown by angle described by PQR. With the cyclopentane shown in this figure, the bisected angle is 54 degrees, so the subsequent bond will be drawn on this line described by the bisection of PQR. For various ring sizes, the value of the bisected angle will vary with the size of the angles of the ring based on the angle between the two bonds connected at the atom where the addition occurs. The same calculation is applied to straight chains, although not shown in a diagram.

Figure 28B:
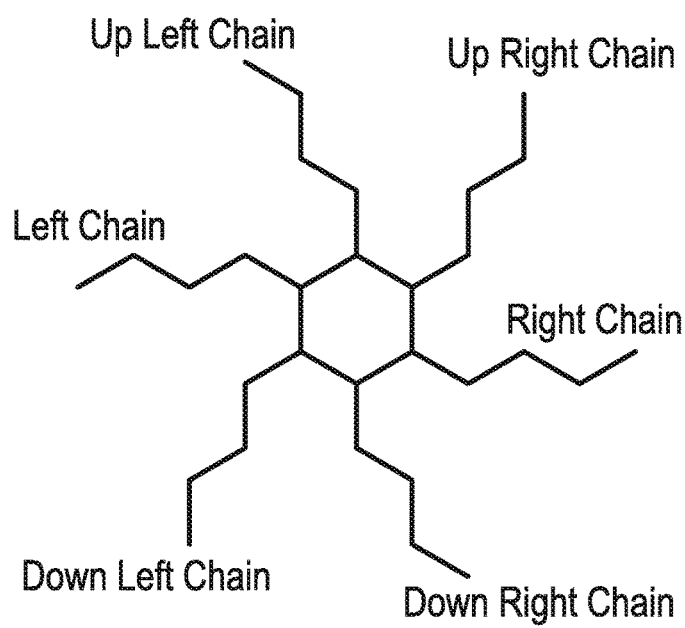
FIG. 28B shows general direction growth of connected atoms originating from a ring.

As shown in FIG. 28B the second connected atom attached will be represented as line vectors are not drawn in any direction, but systematically in vectors alternating by 120 degrees. The general direction with these alternating vectors can be in six directions. Generally, interpretations of swipe gestures resolve directionality in at most four directions: up, down, left and right. This is insufficient to capture the six different directions that may occur in structure drawings for organic molecule representations.

Figure 29:
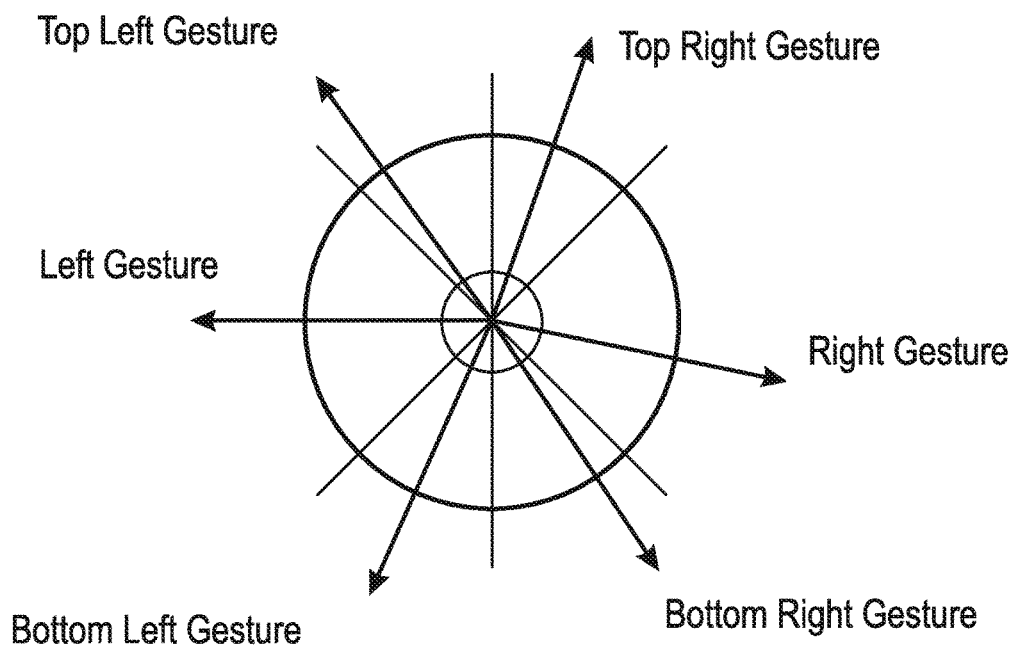
FIG. 29 shows the directions of chain growth from initial touch.
Figure 30:
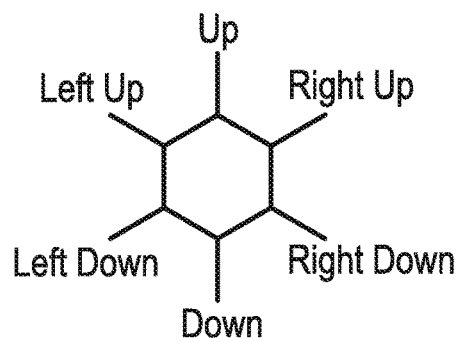
FIG. 30 shows the pairing of the connected atom segment based on the direction of the last line segment.

To enable drawing chains in six directions with a series of swipes requires a new gesture that can accommodate those six directions. As shown in FIG. 29, all directions from an initial touch or click of the screen are divided into six segments. When a movement gesture falls within one of those segments, it is identified by one of the six directional types that are labeled: Left, Right, Top Left, Top Right, Bottom Left, or Bottom Right. As shown in FIG. 30, each gesture is paired with the direction of the last line segment representing a bond in the drawing, which can be one of: Up, Down, Left up, Left down, Right up, Right down, and an interpretation of the user's intent is chosen.

Table 3 pairs a gesture with the last connected bond segment to produce a direction of the next bond segment created on the molecule drawing. Some pairings of gestures with bond segments do not produce an operation due to a gesture conflicting with an expected bond segment, e.g., a Top Left gesture when the last bond segment points Down Right.

TABLE 3

Direction of next bond segment given a particular gesture direction

| Gesture Direction | Last Connected Segment | Extension Direction |
|---|---|---|
| Left Gesture | Up | Left up |
| | Down | Left down |
| | Left up | Left down |
| | Left down | Left right |
| | Right up | No operation |
| | Right down | No operation |
| Right gesture | Up | Right up |
| | Down | Right down |
| | Left up | No operation |
| | Left down | No operation |
| | Right up | Right down |
| | Right down | Right up |
| Top Left gesture | Up | Left up |
| | Down | No operation |
| | Left up | Up |
| | Left down | Left up |
| | Right up | Up |
| | Right down | No operation |
| Top Right gesture | Up | Right up |
| | Down | No operation |
| | Left up | Up |
| | Left down | No operation |
| | Right up | Up |
| | Right down | Right up |
| Bottom Left gesture | Up | No operation |
| | Down | Left down |
| | Left up | Left down |
| | Left down | Down |
| | Right up | No operation |
| | Right down | Down |
| Bottom Right gesture | Up | No operation |
| | Down | Right down |
| | Left up | No operation |
| | Left down | Down |
| | Right up | Right down |
| | Right down | Down |

In order to complete the desired features for a molecular structure or a chemical reaction sequence, an iterative cycle of the gesture, machine response and gesture followed by the machine response may be performed until the desired drawing has been completed.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. The word "exemplary" is used exclusively herein to mean "serving as an example, instance, or illustration." Any implementation described herein as "exemplary" is not necessarily to be construed as preferred or advantageous over other implementations. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper or actual orientation.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A device comprising:
   a display;
   a user interface configured to receive gesture input; and
   a processor wherein the device is configured to:
      electronically detect, with the user interface, at least one gesture input from the user in an approximately circular motion that traces a substantially closed curve without corners about a point on the user interface; and
      display, on a portion of the display, a polygonal shaped chemical structure symbol representing a polygonal ring of carbon atoms in response to the detecting, the polygonal ring having a set number of vertices representing a set number of carbon atoms.

2. The device of claim 1, wherein the device is configured to display a chemical structure symbol representing a saturated ring of carbon atoms in response to the detecting.

3. The device of claim 2, wherein the chemical structure symbol is a regular polygon.

4. The device of claim 3, wherein the device is configured to display a number wheel with a particular number displayed thereon, and wherein the displayed regular polygon has the particular number of vertexes.

5. The device of claim 3, wherein the polygonal shaped chemical structure symbol represents cyclohexane.

6. The device of claim 1, wherein the device is configured to electronically detect two fingertips simultaneously in contact with the user interface and moving in an approximately circular motion.

7. The device of claim 6, wherein the device is configured to display a chemical structure symbol representing an unsaturated ring of carbon atoms in response to the detecting.

8. The device of claim 7, wherein the chemical structure symbol is a regular polygon with line segments or a circle on the interior thereof.

9. The device of claim 8, wherein the polygonal shaped chemical structure symbol represents benzene.

10. A non-transient computer readable medium having instructions stored thereon that cause a device comprising a display, a user interface configured to receive gesture input, and a processor to perform a method comprising the acts of:
electronically detecting, with the user interface, at least one gesture input from the user in an approximately circular motion that traces a substantially closed curve without corners about a point on the user interface; and
displaying, on the display, a polygonal shaped chemical structure symbol representing a polygonal ring of carbon atoms in response to the detecting, the polygonal ring having a set number of vertices representing a pre-selected number of carbon atoms.

11. The non-transient computer readable medium of claim 10, wherein the displaying comprises displaying a chemical structure symbol representing a saturated ring of carbon atoms in response to the detecting.

12. The non-transient computer readable medium of claim 11, wherein the chemical structure symbol is a regular polygon.

13. The non-transient computer readable medium of claim 12, wherein the method further comprises displaying a number wheel with a particular number displayed thereon, and wherein the regular polygon has the particular number of vertexes.

14. The non-transient computer readable medium of claim 12, wherein the polygonal shaped chemical structure symbol represents cyclohexane.

15. The non-transient computer readable medium of claim 10, wherein the detecting comprises detecting two fingertips simultaneously in contact with the user interface and moving in an approximately circular motion.

16. The non-transient computer readable medium of claim 15, wherein the displaying comprises displaying a chemical structure symbol representing an unsaturated ring of carbon atoms in response to the detecting.

17. The non-transient computer readable medium of claim 16, wherein the chemical structure symbol is a regular polygon with line segments or a circle on the interior thereof.

18. The non-transient computer readable medium of claim 17, wherein the polygonal shaped chemical structure symbol represents benzene.

* * * * *